(12) United States Patent
Shin et al.

(10) Patent No.: US 8,945,940 B2
(45) Date of Patent: Feb. 3, 2015

(54) MASS- AND PROPERTY-TUNED VARIABLE MASS LABELING REAGENTS AND ANALYTICAL METHODS FOR SIMULTANEOUS PEPTIDE SEQUENCING AND MULTIPLEXED PROTEIN QUANTIFICATION USING THEREOF

(75) Inventors: Seung Koo Shin, Pohang-si (KR); Jongcheol Seo, Seoul (KR); Min-Soo Suh, Pohang-si (KR); Hye-Joo Yoon, Pohang-si (KR)

(73) Assignee: Postech Academy-Industry Foundation, Pohang-si (KR)

( * ) Notice: Subject to any disclaimer, the term of this patent is extended or adjusted under 35 U.S.C. 154(b) by 231 days.

(21) Appl. No.: 12/601,512

(22) PCT Filed: Jul. 10, 2009

(86) PCT No.: PCT/KR2009/003808
§ 371 (c)(1),
(2), (4) Date: May 24, 2010

(87) PCT Pub. No.: WO2010/008159
PCT Pub. Date: Jan. 21, 2010

(65) Prior Publication Data
US 2011/0071040 A1 Mar. 24, 2011

(30) Foreign Application Priority Data

Jul. 18, 2008 (KR) ........................ 10-2008-0070272
Mar. 6, 2009 (KR) ........................ 10-2009-0019444
Jun. 18, 2009 (KR) ........................ 10-2009-0054540

(51) Int. Cl.
*C07K 5/04* (2006.01)
*C07K 5/06* (2006.01)
(Continued)

(52) U.S. Cl.
CPC ................ *G01R 3/00* (2013.01); *C07B 59/008* (2013.01); *C07C 237/22* (2013.01); *C07K 1/13* (2013.01); *C07K 5/06026* (2013.01);
(Continued)

(58) Field of Classification Search
CPC ........................... C12Q 2563/167; C07K 5/06
USPC ............................................ 930/10; 436/173
See application file for complete search history.

(56) References Cited

U.S. PATENT DOCUMENTS

| 5,360,819 A | 11/1994 | Giese ............................ 514/538 |
| 2003/0228700 A1 | 12/2003 | Peters et al. .................... 436/86 |

(Continued)

FOREIGN PATENT DOCUMENTS

| KR | 10-2006-0001608 | 1/2006 |
| KR | 10-2010-0009466 | 1/2010 |

(Continued)

OTHER PUBLICATIONS

Hologne et al., "Deuterated peptides and proteins in MAS solid-state NMR", 2006, Prog. NMR Spect., pp. 211-232.*
(Continued)

*Primary Examiner* — Christopher M Babic
*Assistant Examiner* — Jeremy C Flinders
(74) *Attorney, Agent, or Firm* — Seed IP Law Group PLLC

(57) ABSTRACT

The present invention provides variable mass labeling reagents, a set of the variable mass labeling reagents, and a multiplexed set of variable mass labeling reagents.

20 Claims, 32 Drawing Sheets

(51) Int. Cl.

| | | |
|---|---|---|
| *G01R 3/00* | (2006.01) | |
| *C07B 59/00* | (2006.01) | |
| *C07C 237/22* | (2006.01) | |
| *C07K 1/13* | (2006.01) | |
| *C07K 5/062* | (2006.01) | |
| *C07K 5/065* | (2006.01) | |
| *C07K 5/072* | (2006.01) | |
| *C07K 5/078* | (2006.01) | |
| *G01N 33/68* | (2006.01) | |
| *G01N 30/72* | (2006.01) | |
| *C40B 20/04* | (2006.01) | |

(52) U.S. Cl.
CPC ........ *C07K 5/06052* (2013.01); *C07K 5/06069* (2013.01); *C07K 5/06078* (2013.01); *C07K 5/06095* (2013.01); *C07K 5/06104* (2013.01); *C07K 5/06139* (2013.01); *G01N 33/6851* (2013.01); *C12Q 2563/167* (2013.01); *C40B 20/04* (2013.01); *G01N 2458/15* (2013.01); *Y10S 930/01* (2013.01)
USPC .................................. 436/173; 930/10; 506/4

(56) References Cited

U.S. PATENT DOCUMENTS

2005/0148087 A1  7/2005  Pappin et al. ................... 436/86
2006/0148093 A1  7/2006  Gygi et al. .................... 436/173

FOREIGN PATENT DOCUMENTS

KR   10-2010-0009479   1/2010
WO   2005/068446      7/2005

OTHER PUBLICATIONS

Staroske et al., J. Mass Spectrom. Soc. Jpn., 1998, 46(1):69-73.*
International Search Report, for International Application No. PCT/KR2009/003808, mailed Feb. 18, 2010, 4 pages.
Seo et al., "Mass-Balanced $^1$H/$^2$H Isotope Dipeptide Tag for Simultaneous Protein Quantitation and Identification," *Anal. Chem.* 80:6145-6153, 2008.
Ross et al., "Multiplexed Protein Quantitation in *Saccharomyces cerevisiae* Using Amine-reactive Isobaric Tagging Reagents," *Molecular & Cellular Proteomics* 3(12):1154-1169, 2004.
Thompson et al., "Tandem Mass Tags: A Novel Quantification Strategy for Comparative Analysis of Complex Protein Mixtures by MS/MS," *Anal. Chem.* 75(8):1895-1904, 2003.
Office Action for Chinese Patent Application No. 200980000431.5, dated Oct. 10, 2012 (15 pages).
Staroske, Thomas et al., "Interactions between Vancomycin and Cell-Wall Precursor Analogs Studied by Electrospray Mass Spectrometry," *J. Mass Spectrom. Soc. Jpn.*, 46(1):69-73 (1998).

* cited by examiner (a)

□ immonium ions   ▨ internal fragments   ■ y-type ions (b)

| Mass-tunable group ($R_T$) | Tagging signature ($b_0$) mass | Quantification signal mass | |
|---|---|---|---|
| | | $^Lb_s$ / $^Hb_s$ | $^La_s$ / $^Ha_s$ |
| $C_1$ (-$CH_3$) | 188 Th | 114 / 117 Th | 86 / 89 Th |
| $C_2$ (-$C_2H_5$) | 202 Th | 128 / 131 Th | 100 / 103 Th |
| $C_3$ (-$C_3H_7$) | 216 Th | 142 / 145 Th | 114 / 117 Th |
| $C_4$ (-$C_4H_9$) | 230 Th | 156 / 159 Th | 128 / 131 Th |
| $C_5$ (-$C_5H_{11}$) | 244 Th | 170 / 173 Th | 142 / 145 Th |
| $C_6$ (-$C_6H_{13}$) | 258 Th | 184 / 187 Th | 156 / 159 Th |
| $C_7$ (-$C_7H_{15}$) | 272 Th | 198 / 201 Th | 170 / 173 Th |
| $C_8$ (-$C_8H_{17}$) | 286 Th | 212 / 215 Th | 184 / 187 Th |

Fig. 6
(a) Solid-Phase Synthesis of Acid Form of MBITs
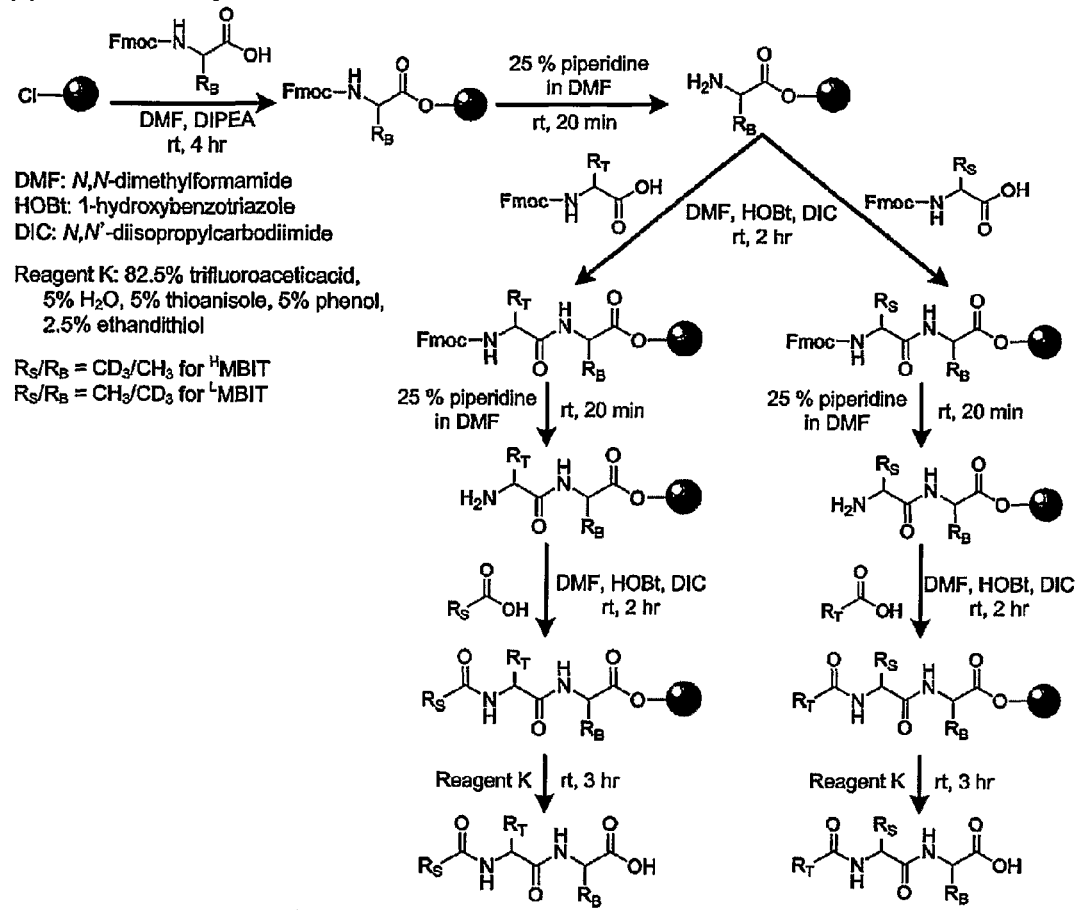
(b) Solution-Phase Synthesis of Acid Form of MBITs
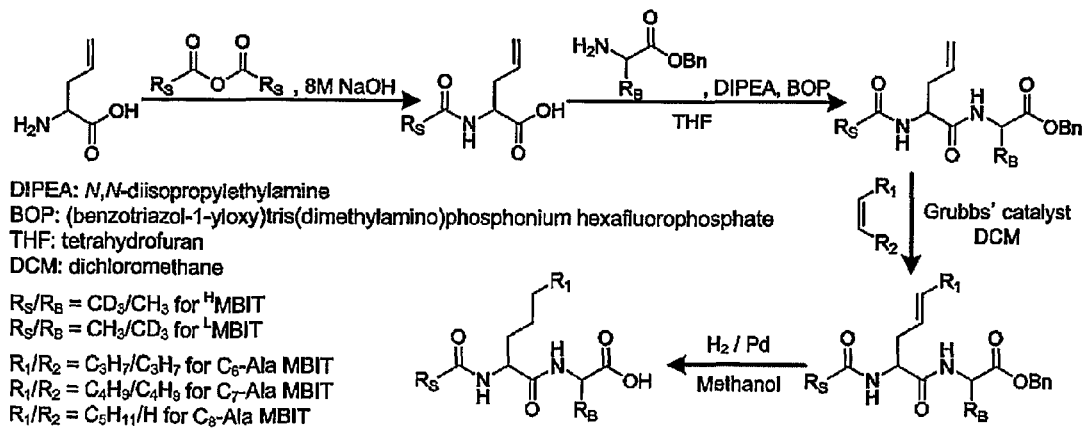

(c) Ac-VA- (d) Ac-QA- (g) Ac-RA- (h) Ac-YA-

Fig. 11
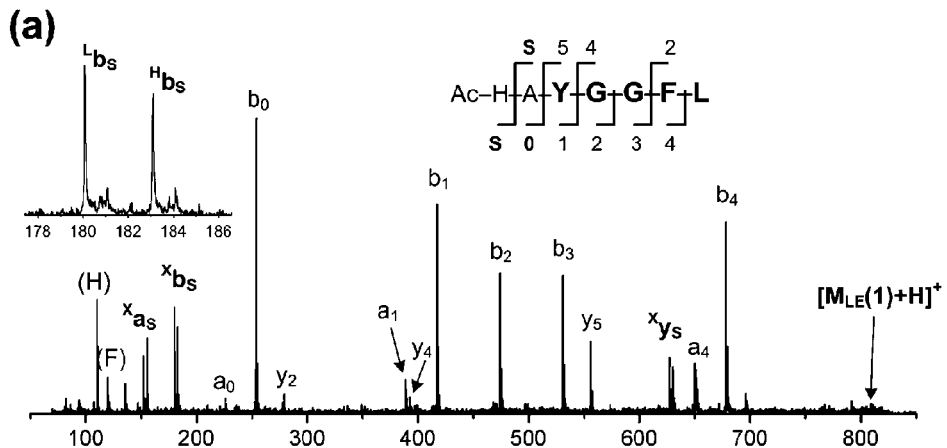
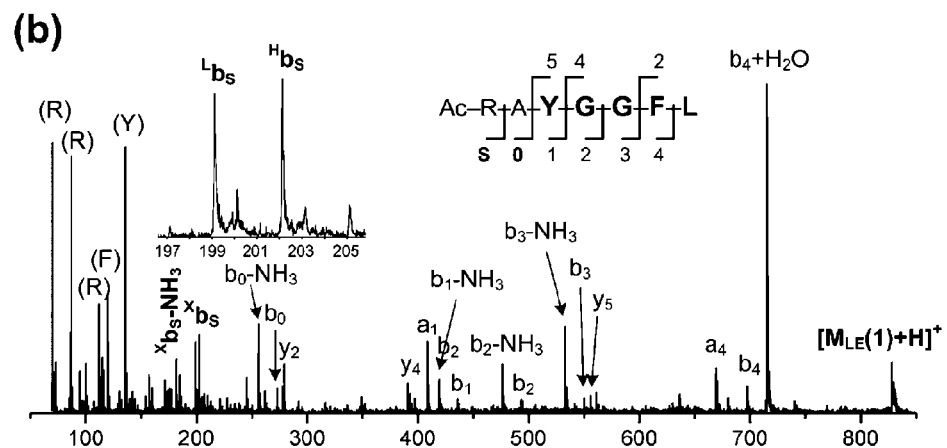
Fig. 12
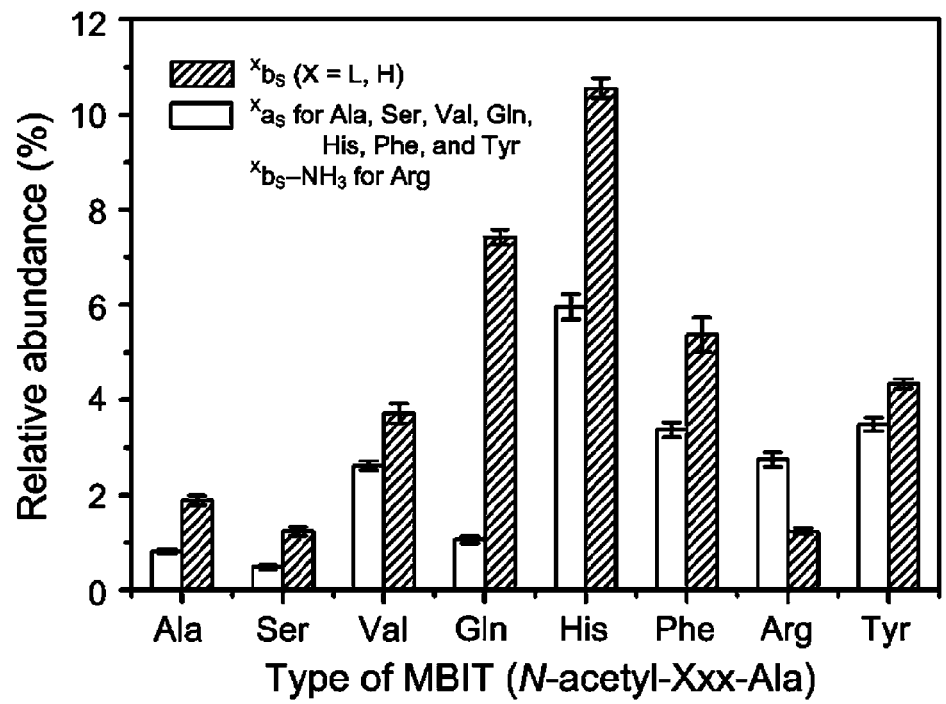

Fig. 14
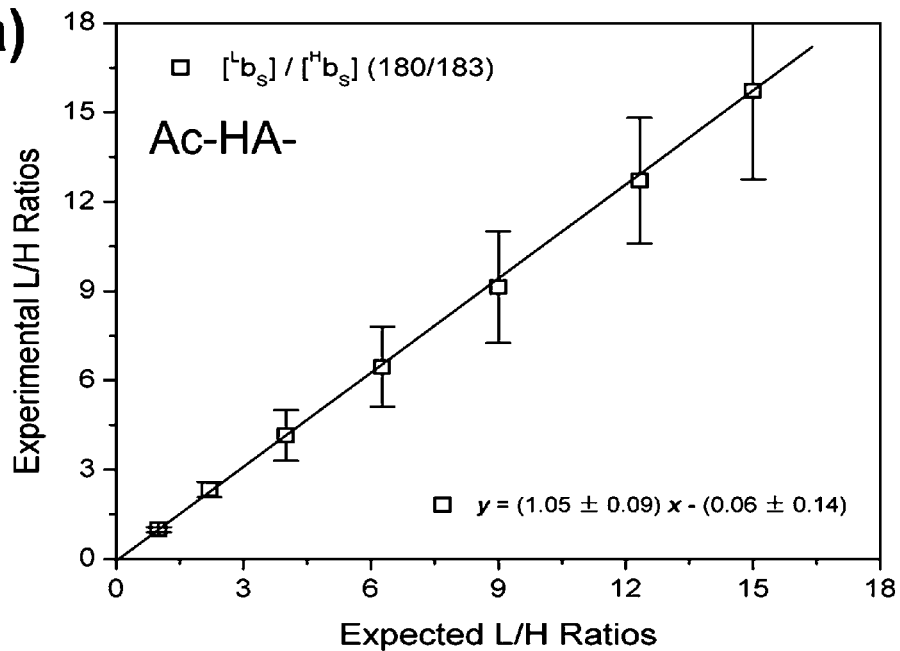
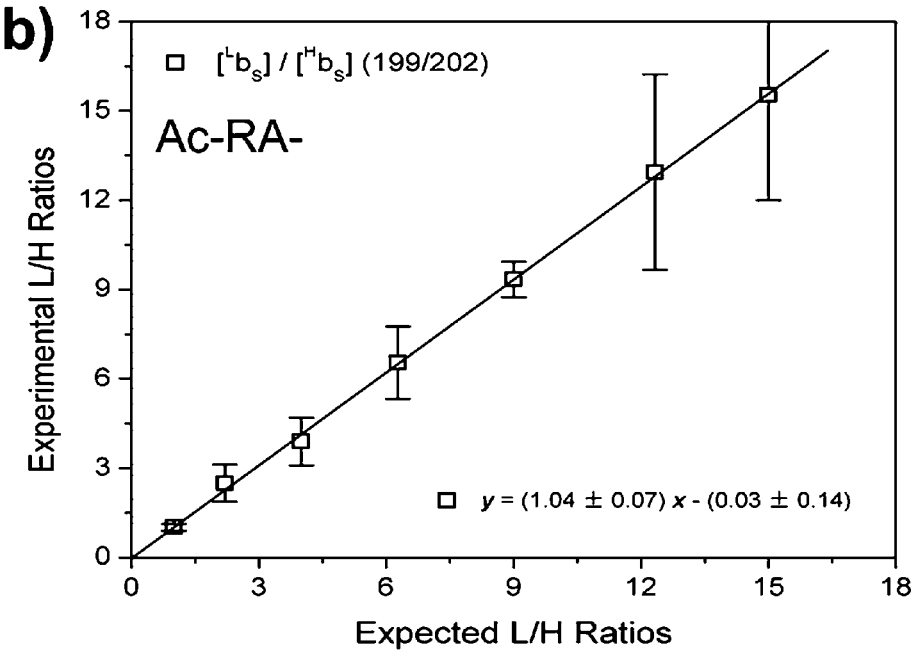

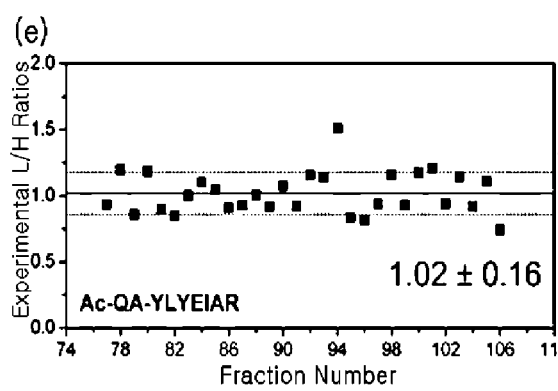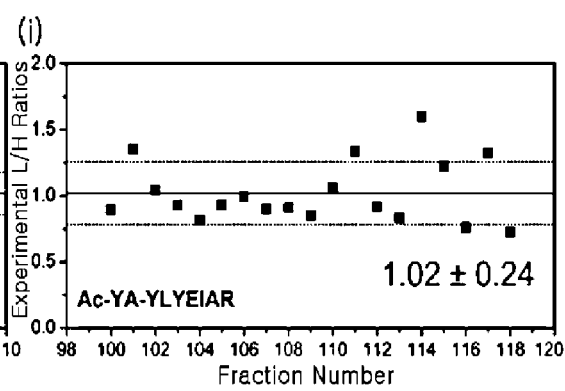
FIG. 16E  FIG. 16I

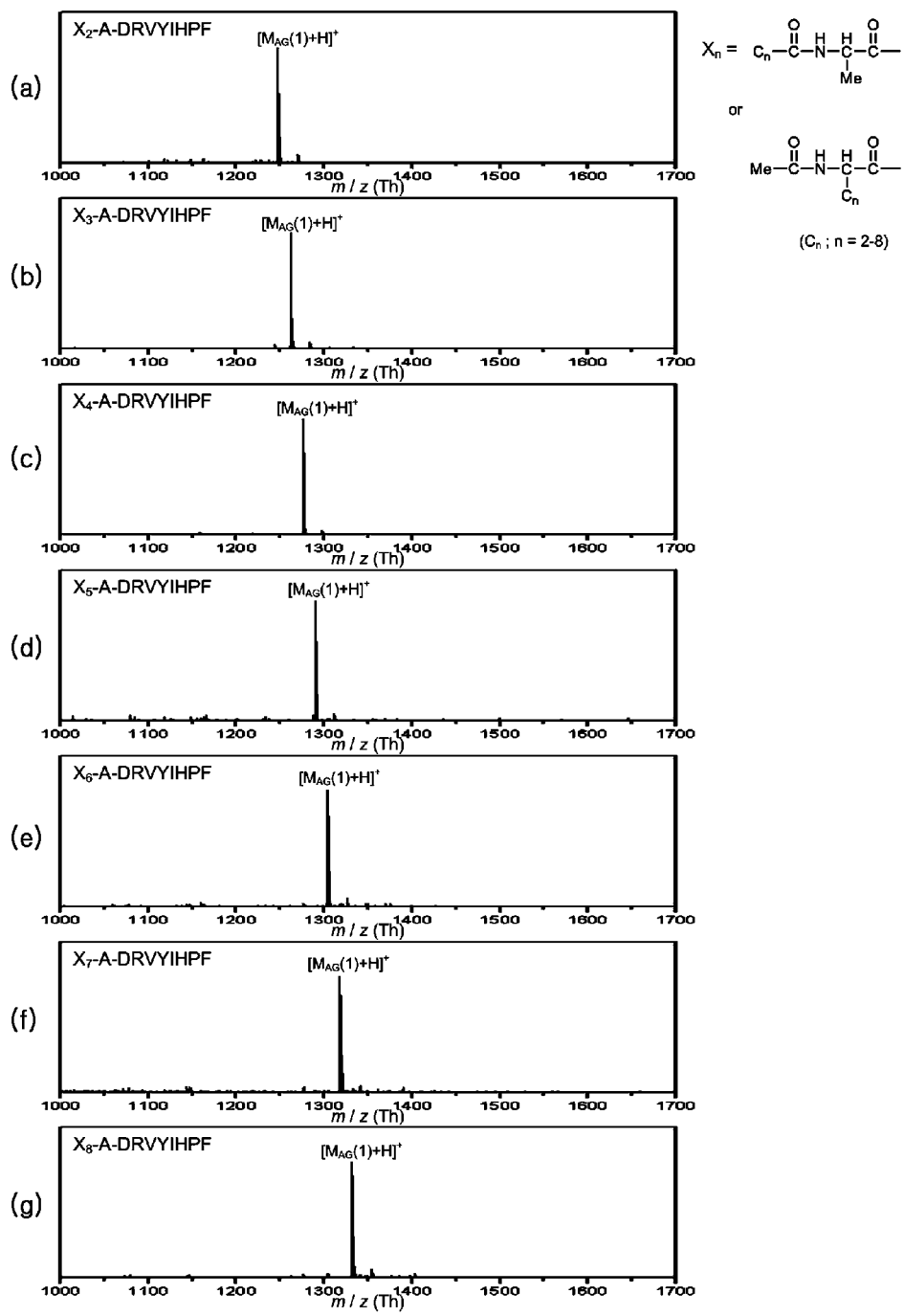

Fig. 20
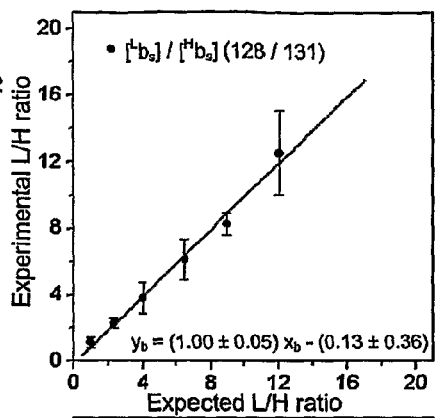
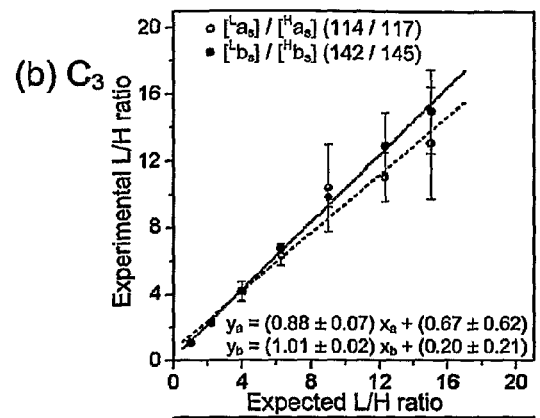
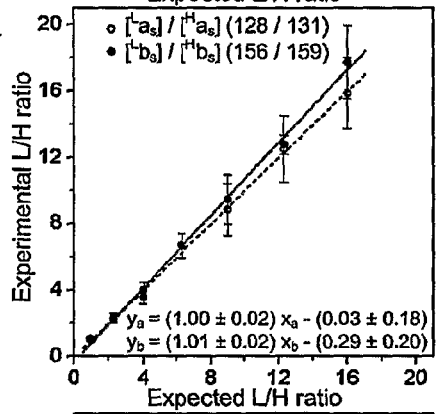
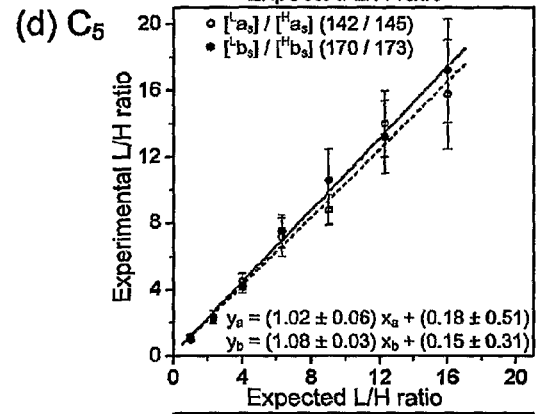
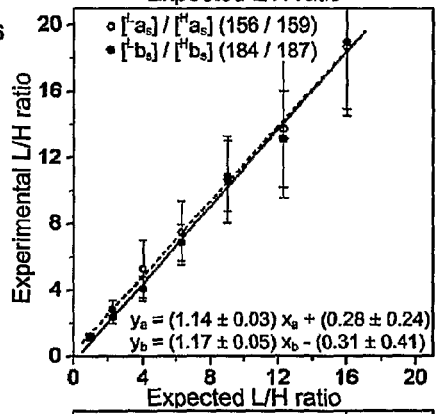
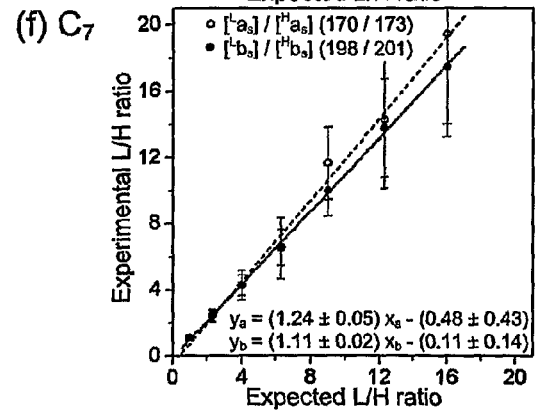
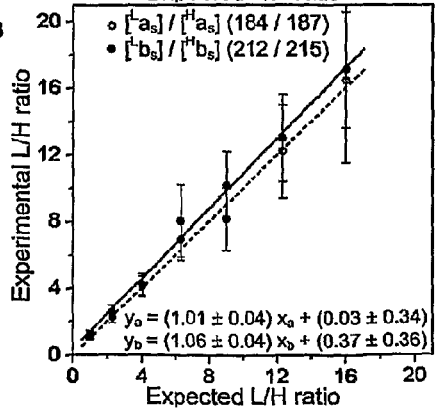

Mass Spectra of Triple 2-plex MBIT-labeled Peptides

1: VLEIR
2: EIFLR
3: LLDAPAAIR
4: QLETEPDLFIR
5: GVVDSEDLPLNLSR

△ : $X_6$-Ala-
□ : $X_7$-Ala-
○ : $X_8$-Ala-

Quadruplex Quantification of Triple 2-plex MBIT-labeled Hsc82p

| | Sequence | De novo sequencing results ($C_6$) | | |
|---|---|---|---|---|
| | | Sequence | SEQ ID NO | Confidence (%) |
| (a) | VLEIR | V*LELR | 9 | 99 |
| | | D*PELR | 10 | <1 |
| | EIFLR | E*LFLR | 13 | 99 |
| | | E*EMLR | 14 | <1 |
| | LLDAPAAIR | L*LDAPAALR | 16 | 63.9 |
| | | L*LDAAPALR | 19 | 34.9 |
| | QLETEPDLFIR | G*ALETEPDLFLR | 22 | 34.3 |
| | | Q*LETEPDLFLR | 25 | 25.2 |
| | GVVDSEDLPLNLSR | G*VVDSEDLRAPLSR | 27 | 99 |
| | | R*VDSEDLRAPLSR | 30 | <1 |

| | Sequence | De novo sequencing results ($C_7$) | | |
|---|---|---|---|---|
| | | Sequence | SEQ ID NO | Confidence (%) |
| (b) | VLEIR | V*LELR | 9 | 99 |
| | | L*VELR | 11 | <1 |
| | EIFLR | E*LFLR | 13 | 95.8 |
| | | E*LYPR | 15 | 2.5 |
| | LLDAPAAIR | L*LDAPASPR | 17 | 52.5 |
| | | L*LDAVRPR | 21 | 33.8 |
| | QLETEPDLFIR | V*DRTEPDLFLR | 24 | 50.3 |
| | | Q*LETEPDLFLR | 25 | 15.6 |
| | GVVDSEDLPLNLSR | G*VVDSEDLPLNLSR | 8 | 42.3 |
| | | G*VVDSEDLLPNLSR | 28 | 36.8 |

| | Sequence | De novo sequencing results ($C_8$) | | |
|---|---|---|---|---|
| | | Sequence | SEQ ID NO | Confidence (%) |
| (c) | VLEIR | V*LELR | 9 | 97.2 |
| | | M*LPLR | 12 | 2.2 |
| | EIFLR | E*LFLR | 13 | 99 |
| | | E*LYPR | 15 | <1 |
| | LLDAPAAIR | L*LDAAAPLR | 18 | 76.8 |
| | | L*LDALAAPR | 20 | 17.9 |
| | QLETEPDLFIR | Q*LETEDPLFLR | 26 | 99 |
| | | L*QETEDPLFLR | 23 | <1 |
| | GVVDSEDLPLNLSR | G*VVDSEDLRAPLSR | 27 | 68.6 |
| | | G*VVDDTDLRAPLSR | 29 | 18.5 |

*Fig. 25*

SEQUENCE LISTING

```
<160> NUMBER OF SEQ ID NOS: 30

<210> SEQ ID NO 1
<211> LENGTH: 7
<212> TYPE: PRT
<213> ORGANISM: Artificial Sequence
<220> FEATURE:
<223> OTHER INFORMATION: SYNTHETIC PEPTIDE

<400> SEQUENCE: 1

Tyr Leu Tyr Glu Ile Ala Arg
 1               5

<210> SEQ ID NO 2
<211> LENGTH: 8
<212> TYPE: PRT
<213> ORGANISM: Artificial Sequence
<220> FEATURE:
<223> OTHER INFORMATION: Angiotensin II

<400> SEQUENCE: 2

Asp Arg Val Tyr Ile His Pro Phe
 1               5

<210> SEQ ID NO 3
<211> LENGTH: 5
<212> TYPE: PRT
<213> ORGANISM: Artificial Sequence
<220> FEATURE:
<223> OTHER INFORMATION: leucine enkephalin

<400> SEQUENCE: 3

Tyr Gly Gly Phe Leu
 1               5
```

```
<210> SEQ ID NO 4
<211> LENGTH: 5
<212> TYPE: PRT
<213> ORGANISM: Artificial Sequence
<220> FEATURE:
<223> OTHER INFORMATION: SYNTHETIC PEPTIDE

<400> SEQUENCE: 4

Val Leu Glu Ile Arg
  1               5

<210> SEQ ID NO 5
<211> LENGTH: 5
<212> TYPE: PRT
<213> ORGANISM: Artificial Sequence
<220> FEATURE:
<223> OTHER INFORMATION: SYNTHETIC PEPTIDE

<400> SEQUENCE: 5

Glu Ile Phe Leu Arg
  1               5

<210> SEQ ID NO 6
<211> LENGTH: 9
<212> TYPE: PRT
<213> ORGANISM: Artificial Sequence
<220> FEATURE:
<223> OTHER INFORMATION: SYNTHETIC PEPTIDE

<400> SEQUENCE: 6

Leu Leu Asp Ala Pro Ala Ala Ile Arg
  1               5

<210> SEQ ID NO 7
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 7

Gln Leu Glu Thr Glu Pro Asp Leu Phe Ile Arg
  1               5                  10

<210> SEQ ID NO 8
<211> LENGTH: 14
<212> TYPE: PRT
<213> ORGANISM: Artificial Sequence
<220> FEATURE:
<223> OTHER INFORMATION: SYNTHETIC PEPTIDE

<400> SEQUENCE: 8

Gly Val Val Asp Ser Glu Asp Leu Pro Leu Asn Leu Ser Arg
  1               5                  10

<210> SEQ ID NO 9
<211> LENGTH: 5
<212> TYPE: PRT
<213> ORGANISM: Artificial Sequence
<220> FEATURE:
<223> OTHER INFORMATION: SYNTHETIC PEPTIDE

<400> SEQUENCE: 9

Val Leu Glu Leu Arg
  1               5
```

```
<210> SEQ ID NO 10
<211> LENGTH: 5
<212> TYPE: PRT
<213> ORGANISM: Artificial Sequence
<220> FEATURE:
<223> OTHER INFORMATION: SYNTHETIC PEPTIDE

<400> SEQUENCE: 10

Asp Pro Glu Leu Arg
 1               5

<210> SEQ ID NO 11
<211> LENGTH: 5
<212> TYPE: PRT
<213> ORGANISM: Artificial Sequence
<220> FEATURE:
<223> OTHER INFORMATION: SYNTHETIC PEPTIDE

<400> SEQUENCE: 11

Leu Val Glu Leu Arg
 1               5

<210> SEQ ID NO 12
<211> LENGTH: 5
<212> TYPE: PRT
<213> ORGANISM: Artificial Sequence
<220> FEATURE:
<223> OTHER INFORMATION: SYNTHETIC PEPTIDE

<400> SEQUENCE: 12

Met Leu Pro Leu Arg
 1               5

<210> SEQ ID NO 13
<211> LENGTH: 5
<212> TYPE: PRT
<213> ORGANISM: Artificial Sequence
<220> FEATURE:
<223> OTHER INFORMATION: SYNTHETIC PEPTIDE

<400> SEQUENCE: 13

Glu Leu Phe Leu Arg
 1               5

<210> SEQ ID NO 14
<211> LENGTH: 5
<212> TYPE: PRT
<213> ORGANISM: Artificial Sequence
<220> FEATURE:
<223> OTHER INFORMATION: SYNTHETIC PEPTIDE

<400> SEQUENCE: 14

Glu Glu Met Leu Arg
 1               5

<210> SEQ ID NO 15
<211> LENGTH: 5
<212> TYPE: PRT
<213> ORGANISM: Artificial Sequence
<220> FEATURE:
<223> OTHER INFORMATION: SYNTHETIC PEPTIDE

<400> SEQUENCE: 15

Glu Leu Tyr Pro Arg
 1               5
```

```
<210> SEQ ID NO 16
<211> LENGTH: 9
<212> TYPE: PRT
<213> ORGANISM: Artificial Sequence
<220> FEATURE:
<223> OTHER INFORMATION: SYNTHETIC PEPTIDE

<400> SEQUENCE: 16

Leu Leu Asp Ala Pro Ala Ala Leu Arg
  1               5

<210> SEQ ID NO 17
<211> LENGTH: 9
<212> TYPE: PRT
<213> ORGANISM: Artificial Sequence
<220> FEATURE:
<223> OTHER INFORMATION: SYNTHETIC PEPTIDE

<400> SEQUENCE: 17

Leu Leu Asp Ala Pro Ala Ser Pro Arg
  1               5

<210> SEQ ID NO 18
<211> LENGTH: 9
<212> TYPE: PRT
<213> ORGANISM: Artificial Sequence
<220> FEATURE:
<223> OTHER INFORMATION: SYNTHETIC PEPTIDE

<400> SEQUENCE: 18

Leu Leu Asp Ala Ala Ala Pro Leu Arg
  1               5

<210> SEQ ID NO 19
<211> LENGTH: 9
<212> TYPE: PRT
<213> ORGANISM: Artificial Sequence
<220> FEATURE:
<223> OTHER INFORMATION: SYNTHETIC PEPTIDE

<400> SEQUENCE: 19

Leu Leu Asp Ala Ala Pro Ala Leu Arg
  1               5

<210> SEQ ID NO 20
<211> LENGTH: 9
<212> TYPE: PRT
<213> ORGANISM: Artificial Sequence
<220> FEATURE:
<223> OTHER INFORMATION: SYNTHETIC PEPTIDE

<400> SEQUENCE: 20

Leu Leu Asp Ala Leu Ala Ala Pro Arg
  1               5

<210> SEQ ID NO 21
<211> LENGTH: 8
<212> TYPE: PRT
<213> ORGANISM: Artificial Sequence
<220> FEATURE:
<223> OTHER INFORMATION: SYNTHETIC PEPTIDE

<400> SEQUENCE: 21

Leu Leu Asp Ala Val Arg Pro Arg
  1               5
```

```
<210> SEQ ID NO 22
<211> LENGTH: 12
<212> TYPE: PRT
<213> ORGANISM: Artificial Sequence
<220> FEATURE:
<223> OTHER INFORMATION: SYNTHETIC PEPTIDE

<400> SEQUENCE: 22

Gly Ala Leu Glu Thr Glu Pro Asp Leu Phe Leu Arg
 1               5                  10

<210> SEQ ID NO 23
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 23

Leu Gln Glu Thr Glu Asp Pro Leu Phe Leu Arg
 1               5                  10

<210> SEQ ID NO 24
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 24

Val Asp Arg Thr Glu Pro Asp Leu Phe Leu Arg
 1               5                  10

<210> SEQ ID NO 25
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 25

Gln Leu Glu Thr Glu Pro Asp Leu Phe Leu Arg
 1               5                  10

<210> SEQ ID NO 26
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 26

Gln Leu Glu Thr Glu Asp Pro Leu Phe Leu Arg
 1               5                  10

<210> SEQ ID NO 27
<211> LENGTH: 14
<212> TYPE: PRT
<213> ORGANISM: Artificial Sequence
<220> FEATURE:
<223> OTHER INFORMATION: SYNTHETIC PEPTIDE

<400> SEQUENCE: 27

Gly Val Val Asp Ser Glu Asp Leu Arg Ala Pro Leu Ser Arg
 1               5                  10
```

```
<210> SEQ ID NO 28
<211> LENGTH: 14
<212> TYPE: PRT
<213> ORGANISM: Artificial Sequence
<220> FEATURE:
<223> OTHER INFORMATION: SYNTHETIC PEPTIDE

<400> SEQUENCE: 28

Gly Val Val Asp Ser Glu Asp Leu Leu Pro Asn Leu Ser Arg
 1               5                  10

<210> SEQ ID NO 29
<211> LENGTH: 14
<212> TYPE: PRT
<213> ORGANISM: Artificial Sequence
<220> FEATURE:
<223> OTHER INFORMATION: SYNTHETIC PEPTIDE

<400> SEQUENCE: 29

Gly Val Val Asp Asp Thr Asp Leu Arg Ala Pro Leu Ser Arg
 1               5                  10

<210> SEQ ID NO 30
<211> LENGTH: 13
<212> TYPE: PRT
<213> ORGANISM: Artificial Sequence
<220> FEATURE:
<223> OTHER INFORMATION: SYNTHETIC PEPTIDE

<400> SEQUENCE: 30

Arg Val Asp Ser Glu Asp Leu Arg Ala Pro Leu Ser Arg
 1               5                  10
```

MASS- AND PROPERTY-TUNED VARIABLE MASS LABELING REAGENTS AND ANALYTICAL METHODS FOR SIMULTANEOUS PEPTIDE SEQUENCING AND MULTIPLEXED PROTEIN QUANTIFICATION USING THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 760173_402_USPC_SEQUENCE LISTING.txt. The text file is 6 KB, was created on Oct. 14, 2011, and is being submitted electronically via EFS-Web.

TECHNICAL FIELD

The present invention relates to variable mass labeling reagents and analysis methods for simultaneous peptide sequencing and protein quantitation using the same, more particularly, variable mass labeling reagents comprising hydrogen isotopes, which provides tunability in property and mass to display differential quantitation signals at different mass regions, and analysis methods for simultaneous peptide sequencing and multiplexed protein quantitation using the same.

BACKGROUND ART

Mass spectrometry has been widely used for sequencing and quantitation of proteins and peptides. To identify proteins, for instance, peptides produced by enzyme digestion are ionized by either Matrix-Assisted Laser Desorption/Ionization(MALDI) or Electrospray Ionization(ESI), and then their masses can be measured by means of a mass spectrometer to characterize the protein. More exactly, some peptides are further cleaved into fragments to identify the peptide sequence.

For the quantification of proteins and peptides by mass spectrometry, a number of stable isotope tags have been chemically introduced as markers into proteins or peptides of interest. Chemical tags differentially labeled with isotopes are incorporated into the same samples to be analyzed, and the mass of each sample can be distinguished due to the mass difference of the isotopes in the resulting mass spectra or tandem mass spectra, thus allowing protein quantification by the comparison of their relative intensities.

Recently, the isobaric chemical tagging strategy has been used for simultaneous protein quantitation and sequencing. In US 2005/0148087 and WO 2005/068446, disclosed are isobaric reagents labeled with isotopes, which bind with peptide to display quantitation signals in tandem mass spectrometry. However, the labeling reagents used in the known methods are problematic in that expensive carbon, nitrogen and oxygen isotopes are used, thus carrying high cost. In addition, another drawback is that because of the limited signal mass window, unexpected chemical noise may hinder the analysis. Therefore, there is a need for novel isobaric labeling reagents incorporating low-cost hydrogen isotopes for simultaneous peptide sequencing and protein quantitation. Further, there is a need for novel isobaric variable mass labeling reagents that provide tunability not only in mass window of quantitation signals but also in property of peptides, thus applicable to a wide range of biomolecules.

The present inventors have suggested a novel isobaric labeling reagent based on dipeptide, mass-balanced $^1H/^2H$-isotope tag (MBIT) which only employs hydrogen isotopes and offers tunability in quantitation signal mass window, disclosed in Korean Patent Application No. 2008-0070272. Further, they have demonstrated that the replacement of the mass-tunable group of the 2-plex isobaric labeling reagent with other natural amino acid side chains having various properties offers possibilities of tuning the signal mass window and its property, disclosed in Korean Patent Application No. 2009-0019444. Various MBITs having different amino acid side chains showed up to ten-fold difference in the quantitation signal intensities due to dissimilar chemical properties of the amino acid side chains. To achieve better performance of the MBIT reagents in simultaneous multiplexed quantitation, it is necessary to use the MBIT reagents having similar chemical properties but different quantitation signals in a combination of two or more thereof. Accordingly, for simultaneous multiplexed protein quantification, a variety of MBIT reagents having identical property is needed to provide similar quantitation signal intensity. Thus, they have suggested mass- and property-tuned variable mass isobaric labeling reagents, a set of the labeling reagents, and analysis methods for simultaneous quantitation, disclosed in Korean Patent Application No. 10-2009-0054540.

DISCLOSURE OF INVENTION

Technical Problem

Taken together, it is intended to provide isobaric labeling reagents for simultaneous peptide sequencing and multiplexed protein quantitation, providing the tunability in mass and property by using natural or artificial amino acids, and analysis methods for simultaneous multiplexed protein quantification using multiple 2-plex isobaric tags.

Technical Solution

It is an object of the present invention to provide novel isobaric labels for simultaneous peptide sequencing and protein quantitation, comprising isotopes.

It is another object of the present invention to provide isobaric labels for simultaneous peptide sequencing and protein quantitation, comprising hydrogen isotopes.

It is still another object of the present invention to provide variable mass labeling reagents that are composed of two or more isobaric labels for simultaneous peptide sequencing and protein quantitation comprising hydrogen isotopes.

It is still another object of the present invention to provide isobaric variable mass labels for simultaneous peptide sequencing and protein quantitation, comprising hydrogen isotopes and providing the tunability in mass by using natural or artificial amino acids.

It is still another object of the present invention to provide a set of variable mass labeling reagents that is composed of two or more isobaric labels for simultaneous peptide sequencing and protein quantitation, comprising hydrogen isotopes and providing the tunability in mass by using natural or artificial amino acids.

It is still another object of the present invention to provide a set of variable mass labeling reagents that is composed of two or more isobaric labels for simultaneous peptide sequencing and protein quantitation, comprising hydrogen isotopes and providing the tunability in mass by using natural or artificial amino acids to display quantitation signals at different mass regions.

It is still another object of the present invention to provide a set of variable mass labeling reagents that is composed of two or more isobaric labels for simultaneous peptide sequencing and protein quantitation, comprising hydrogen isotopes and providing the tunability in mass by using natural or artificial amino acids with identical properties.

It is still another object of the present invention to provide a set of variable mass labeling reagents that is composed of two or more isobaric labels for simultaneous peptide sequencing and protein quantitation, comprising hydrogen isotopes and providing the tunability in mass by using natural or artificial amino acids with identical properties to display similar quantitation signal intensities at different mass regions.

It is still another object of the present invention to provide analysis methods for simultaneous peptide sequencing and protein quantitation using the set of isobaric variable mass labeling reagents comprising hydrogen isotopes.

It is still another object of the present invention to provide analysis methods for simultaneous peptide sequencing and multiplexed protein quantitation using combination of various 2-plex sets of isobaric variable mass labeling reagents comprising hydrogen isotopes and providing the tunability in mass.

The above and other objects of the present invention can be achieved by the following descriptions.

Advantageous Effects

The present invention provides variable mass labeling reagents comprising hydrogen isotopes and providing the tunability in mass and property to display quantitation signals at different mass regions, a set of variable mass labeling reagents, a multiplexed set of variable mass labeling reagents, analysis methods for simultaneous peptide sequencing and protein quantitation using the set of isobaric variable mass labeling reagents comprising hydrogen isotopes, and analysis methods for simultaneous peptide sequencing and multiplex protein quantitation using the set of variable mass labeling reagents.

BRIEF DESCRIPTION OF DRAWINGS

FIG. 6 is a schematic diagram showing the process of synthesis of MBIT reagents using (a) the solid-phase synthesis and (b) the solution-phase synthesis.

FIG. 11 is a diagram showing the results of tandem mass spectrometry of leucine enkephalin ion ($[M_{LE}(1)+H]^+$, herein $H^+$ is attached) detected after coupling with MBIT. In the N-acetylated dipeptide MBIT reagent (Ac-Xxx-Ala), when Xxx having a mass-tunable group is basic (a) histidine and (b) arginine, the results are shown.

FIG. 12 is a diagram showing the ratio of quantitation signal ($^Xb_S$, X=H or L) intensity according to the mass-tunable group of N-acetylated dipeptide MBIT reagent, and quantitation signal intensity of fragment ions ($^Xa_S$ or $^Xb_S$-$NH_3$) relative to total sum of all fragment ion intensities. Error bars stand for standard deviations from eight repeated experiments.

FIG. 14 is a diagram showing standard quantitation curve obtained by tandem mass spectrometry of the mixtures of different ratio of MBIT reagent-linked leucine enkephalin. In the N-acetylated dipeptide MBIT reagent (Ac-Xxx-Ala), when Xxx having a mass-tunable group is basic (a) histidine and (b) arginine, the results are shown.

In FIG. 16, (a) shows the result of liquid chromatography of eight different pairs of MBIT-tagged YLYEIAR peptides. Also, FIG. 16 is a diagram showing the result of MALDI tandem mass spectrometry of each fraction detected from chromatography of pairs of MBIT-linked YLYEIAR in case that a mass-tunable group is (b) alanine, (c) serine, (d) valine, (e) glutamine, (f) histidine, (g) phenylalanine, (h) arginine, and (i) tyrosine side chains. From the result of quantitation analysis, the mean and standard deviations are given.

FIG. 17 is the results of MALDI mass spectrometry of angiotensin II linked with seven pairs of alkyl group MBIT reagents. The MALDI mass spectra of MBIT reagents having a mass-tunable group ($R_T=C_n$) of (a) ethyl ($C_2$), (b) propyl ($C_3$), (c) butyl ($C_4$), (d) pentyl ($C_5$), (e) hexyl ($C_6$), (f) heptyl ($C_7$), and (g) octyl ($C_8$) are shown. ($X_n$ is N-acetylated amino acid or N-acyl-Ala amino acid having a mass-tunable group of $C_n$).

FIG. 20 is a diagram showing comparison of quantitation linearity in various alkyl group MBITs, in which $^L$MBIT-linked angiotensin II and $^H$MBIT-linked angiotensin II are mixed in a various mixing ratio, and experimental ratios and expected ratios are used to obtain quantitation linearity.

FIG. 25 is the results of de novo sequencing from MALDI tandem mass spectrometry of five types of analytes that were labeled with MBIT having a mass-tunable group ($R_T=C_n$) of (a) hexyl ($C_6$), (b) heptyl($C_7$), and (c) octyl ($C_8$). Underlined amino acids mean that their sequences are verified. Amino acids marked with star represent MBIT-labeled amino acids.

BEST MODE FOR CARRYING OUT THE INVENTION

Figure 1:
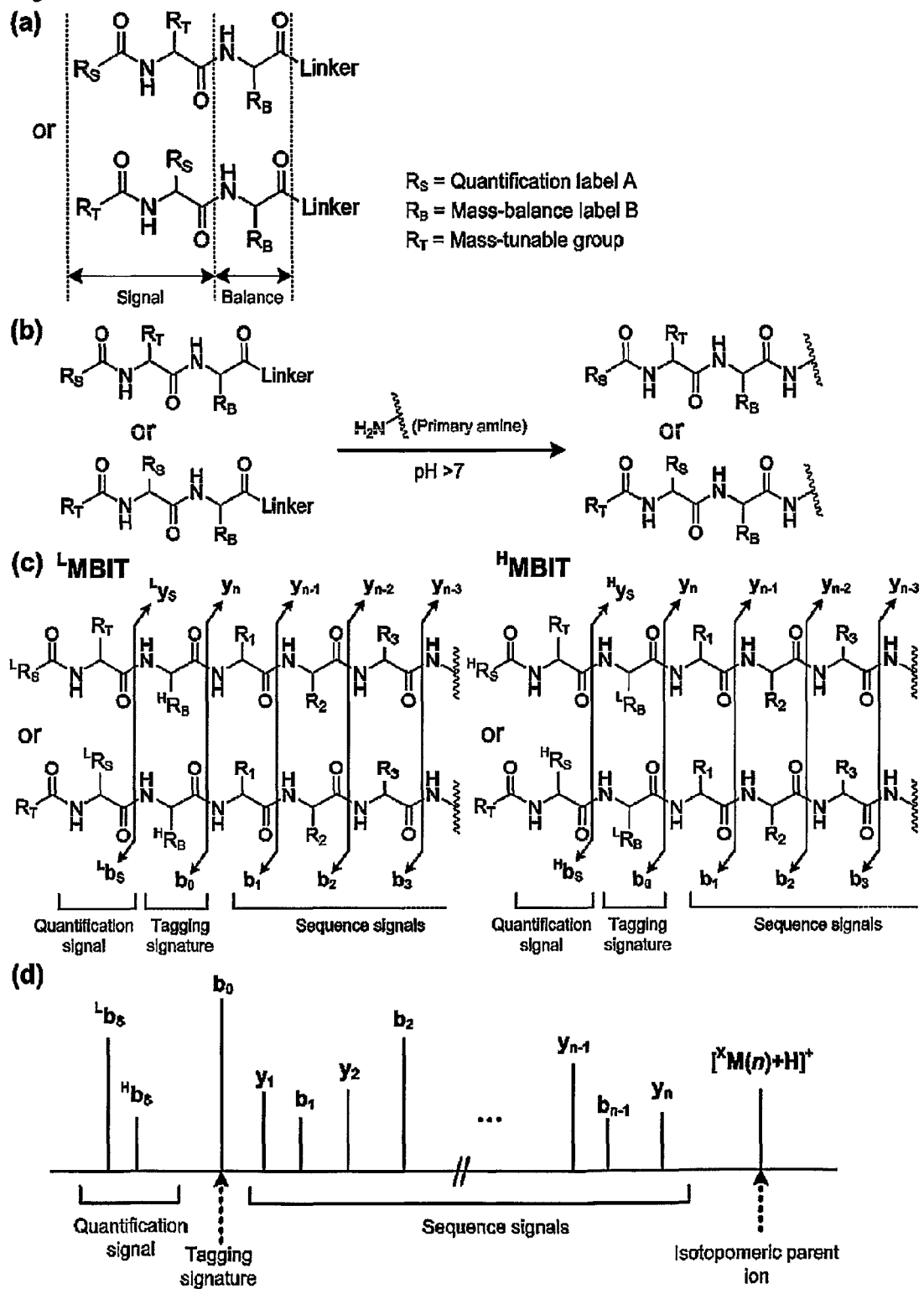
FIG. 1 is a schematic diagram showing the basic concept of MBIT reagent and strategy, in which (a) shows the structure of MBIT reagent, (b) shows the labeling process by coupling MBIT reagent to primary amines, (c) shows the expected fragment ions of MBIT-linked peptides by tandem mass spectrometry, and (d) shows the tandem mass spectra.

The present invention provides variable mass labeling reagents, represented by the following Formula 1.

[Formula 1]

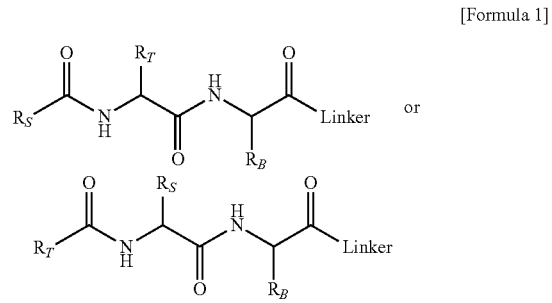

Wherein $R_S$ and $R_B$ are each straight or branched chain $C_1$-$C_{18}$ alkyl; at least one of $R_s$ and $R_B$ contains one or more deuterium atoms; $R_T$ is a mass-tunable group; and Linker is a reactive linker that induces the reaction with an analyte.

As used herein, the term "reactive linker" means an active ester, which becomes a leaving group by nucleophilic attack of amine. The amine is a primary amine. In addition, the reactive linker may be selected from the group consisting of N-hydroxysuccinimidyl group, N-hydroxysulfosuccinimidyl group, benzotriazol-1-yloxyl group, pentahalobenzyl group, 4-nitrophenyl group, and 2-nitrophenyl group. In an embodiment of the present invention, N-hydroxysuccinimidyl group was used as a linker.

As used herein, the term "mass-tunable group" means a group that binds with an analyte and functions to prevent the quantitation signal from overlapping with other fragments in tandem mass spectra by tuning the mass of N-acylated amino acid fragments. The quantitation signal mass window can be tuned by changing $R_T$. The mass-tunable group is a side chain of natural or artificial amino acid residues.

The side chain of the natural amino acid in the mass-tunable group may be the side chain of alanine(Ala), serine (Ser), histidine(His), valine(Val), glutamine(Gln), phenylalanine(Phe), arginine(Arg), or tyrosine(Tyr).

Further, the mass-tunable group may be straight or branched chain $C_2$-$C_{18}$ alkyl, and straight or branched chain alkyl such as ethyl, propyl, butyl, pentyl, hexyl, heptyl, and octyl to embed similar or identical chemical properties.

The $R_S$ and $R_B$ contain deuterium atoms, which allows quantitation analysis based on mass difference of the isotopes. Therefore, the $R_S$ and $R_B$ are each straight or branched chain $C_1$-$C_{18}$ alkyl, and at least one of $R_S$ and $R_B$ contains one or more deuterium atoms. It is preferable that the $R_S$ and $R_B$ are methyl or methyl containing one or more deuterium atoms. The $R_S$ and $R_B$ are composed of alkyl having the same number of carbon atoms, but different number of deuterium atoms. In this regard, it is preferable that the $R_S$ and $R_B$ are each $CH_3$ and $CD_3$ or $CD_3$ and $CH_3$. That is, in the compound, if $R_S$ is $CH_3$, $R_B$ is $CD_3$, or if $R_B$ is $CH_3$, $R_S$ is $CD_3$.

The Formula 1 represents an N-acylated dipeptide having isotopes and a C-terminal amine-reactive linker as a living group by nucleophilic attack. In addition, the dipeptide is a deuterated dipeptide.

Further, the present invention provides a set of variable mass labeling reagents, comprising two or more variable mass labeling reagents represented by Formula 1.

The set of variable mass labeling reagents consists of a pair of two different compounds represented by Formula 1. Since a pair of compounds contains a specific number of deuterium atoms in $R_S$ and $R_B$, the mass of each sample can be distinguished due to the mass difference of the isotopes in the resulting tandem mass spectra, thus allowing protein quantification by the comparison of their relative intensities. In this regard, it is preferable that each of $R_S$ and $R_B$ in two variable mass labeling reagents contains a different number of deuterium atoms, and the two variable mass labeling reagents contain the same number of deuterium atoms.

If $R_S$ contains deuterium atoms more than $R_B$ in compound 1, $R_B$ contains deuterium atoms more than $R_s$ in compound 2. Consequently, the total mass of compound 1 and 2 are the same as each other. In an embodiment of the present invention, a pair of the compound having each $CH_3$ and $CD_3$ in $R_S$ and $R_B$ and the compound having each $CD_3$ and $CH_3$ in $R_S$ and $R_B$ was synthesized.

Further, the present invention provides a multiplexed set of variable mass labeling reagents, comprising two or more sets of variable mass labeling reagents.

Further, the present invention provides a mixture comprising an analyte labeled with the variable mass labeling reagent, a salt thereof or a hydrate thereof. In an embodiment of the present invention, the amine-reactive linker functions as a leaving group to link the compound with an analyte.

In this connection, the analyte may be a protein, a carbohydrate or a lipid. Further, the analyte may be a peptide. Furthermore, the analyte may be a nucleic acid or a derivative thereof, or the analyte may be a steroid.

Further, the present invention provides an analysis method for simultaneous peptide sequencing and protein quantitation, comprising the steps of:

coupling an analyte with the set of variable mass labeling reagents; and quantitating the analyte by fragmentation of the variable mass labeling reagent-linked analyte.

In this connection, the fragmentation for quantitation is performed by tandem mass spectrometry.

The tandem mass spectrometry is characterized in that the quantitation signal mass window is shifted by changing the mass-tunable group of the labeling reagent.

The quantitation signal is one or more fragment ions selected from the group consisting of $b_S$ ion, $a_S$ ion, ($b_S$-$NH_3$) ion, $y_S$ ion, and internal fragment ions containing $R_B$.

If the mass-tunable group is a natural amino acid side chain, the quantitation signal and the tagging signature are as follows.

In the case where the mass-tunable group is a methyl group, the quantitation signals ($b_S$) appear at 114 and 117 Th, the other quantitation signals ($a_S$) appear at 86 and 89 Th, and the tagging signature appears at 188 Th.

In the case where the mass-tunable group is the side chain of serine, the quantitation signals ($b_S$) appear at 130 and 133 Th, the other quantitation signals ($a_S$) appear at 102 and 105 Th, and the tagging signature ($b_0$) appears at 204 Th.

In the case where the mass-tunable group is the side chain of valine, the quantitation signals ($b_S$) appear at 142 and 145 Th, the other quantitation signals ($a_S$) appear at 114 and 117 Th, and the tagging signature ($b_0$) appears at 216 Th.

In the case where the mass-tunable group is the side chain of glutamine, the quantitation signals ($b_S$) appear at 171 and 174 Th, the other quantitation signals ($a_S$) appear at 143 and 146 Th, and the tagging signature ($b_0$) appears at 245 Th.

In the case where the mass-tunable group is the side chain of histidine, the quantitation signals ($b_S$) appear at 180 and 183 Th, the other quantitation signals ($a_S$) appear at 152 and 155 Th, and the tagging signature ($b_0$) appears at 254 Th.

In the case where the mass-tunable group is the side chain of phenylalanine, the quantitation signals ($b_S$) appear at 190 and 193 Th, the other quantitation signals ($a_S$) appear at 162 and 165 Th, and the tagging signature ($b_0$) appears at 264 Th.

In the case where the mass-tunable group is the side chain of arginine, the quantitation signals ($b_S$) appear at 199 and 202 Th, the other quantitation signals ($b_S$-$NH_3$) appear at 182 and 185 Th, and the tagging signature ($b_0$) appears at 273 Th.

In the case where the mass-tunable group is the side chain of tyrosine, the quantitation signals ($b_S$) appear at 206 and 209 Th, the other quantitation signals ($a_S$) appear at 178 and 181 Th, and the tagging signature ($b_0$) appears at 280 Th.

If the mass-tunable group is an artificial amino acid side chain, the quantitation signal and the tagging signature are as follows.

In the case where the mass-tunable group is an ethyl group, the quantitation signals ($b_S$) appear at 128 and 131 Th, the other quantitation signals ($a_S$) appear at 100 and 103 Th, and the tagging signature ($b_0$) appears at 202 Th.

In the case where the mass-tunable group is a straight or branched chain propyl group, the quantitation signals ($b_S$) appear at 142 and 145 Th, the other quantitation signals ($a_S$) appear at 114 and 117 Th, and the tagging signature ($b_0$) appears at 216 Th.

In the case where the mass-tunable group is a straight or branched chain butyl group, the quantitation signals ($b_S$) appear at 156 and 159 Th, the other quantitation signals ($a_S$) appear at 128 and 131 Th, and the tagging signature ($b_0$) appears at 230 Th.

In the case where the mass-tunable group is a straight or branched chain pentyl group, the quantitation signals ($b_S$) appear at 170 and 173 Th, the other quantitation signals ($a_S$) appear at 142 and 145 Th, and the tagging signature ($b_0$) appears at 244 Th.

In the case where the mass-tunable group is a straight or branched chain hexyl group, the quantitation signals ($b_S$) appear at 184 and 187 Th, the other quantitation signals ($a_S$) appear at 156 and 159 Th, and the tagging signature ($b_0$) appears at 258 Th.

In the case where the mass-tunable group is a straight or branched chain heptyl group, the quantitation signals ($b_S$)

appear at 198 and 201 Th, the other quantitation signals ($a_S$) appear at 170 and 173 Th, and the tagging signature ($b_0$) appears at 272 Th.

In the case where the mass-tunable group is a straight or branched chain octyl group, the quantitation signals ($b_S$) appear at 212 and 215 Th, the other quantitation signals ($a_S$) appear at 184 and 187 Th, and the tagging signature ($b_0$) appears at 286 Th.

Further, the present invention provides an analysis method for simultaneous peptide sequencing and protein quantitation, characterized in that the multiplexed set of variable mass labeling reagents is linked to different analytes, followed by fragmentation and quantitation of the analyte.

Further, the present invention provides an analysis method for multiplexed protein quantitation, in which one sample and other different samples are separately quantitated by differential quantitation signal mass depending on the mass-tunable group, during quantitation process of coupling of the analyte with the multiplexed set of variable mass labeling reagents according to the present invention.

Hereinbelow, the present invention will be described in detail with reference to the accompanying drawings.

FIG. 1 is a schematic diagram showing the basic concept of MBIT reagent and strategy, in which (a) shows the structure of MBIT reagent, (b) shows the labeling process by coupling MBIT reagent to primary amines, (c) shows the expected fragment ions of MBIT-linked peptides by tandem mass spectrometry, and (d) shows the tandem mass spectra.

As shown in FIG. 1, the compound 1 according to the present invention is, not theoretically limited to, an N-acylated dipeptide with a C-terminal amine-reactive linker, and its functions are as described in FIG. 1(a).

The compounds are able to bind with the analyte by conjugation with primary amines of target peptides, as depicted in FIG. 1(b). In a pair of MBITs, each MBIT has the same formula, except for the deuterated part, and is conveniently expressed as $^H$MBIT and $^L$MBIT (H: heavy and L: light), in which $^H$MBIT has deuterated $R_S$ and $^L$MBIT has deuterated $R_B$. The total masses of $^L$MBIT and $^H$MBIT-linked analytes are the same with each other. However, of the fragments in tandem mass spectra, the fragments containing only any one of $R_S$ or $R_B$ have differential signal mass from each other depending on $^L$MBIT and $^H$MBIT, and appear at different regions of spectra, as $b_S$ ions shown in FIG. 1(c-d). The relative intensities of the peaks can be quantitated as the relative amounts of the MBIT-linked analytes. On the contrary, the fragments containing both or none of $R_S$ and $R_B$ have constant signal mass, irrespective of $^L$MBIT and $^H$MBIT, and $b_0$ ions as well as $b_S$ ions are detected in the spectra. The $b_0$ ions constantly appear in the spectra, irrespective of $^L$MBIT and $^H$MBIT, and serve as the tagging signature for MBIT conjugation.

Figure 2:
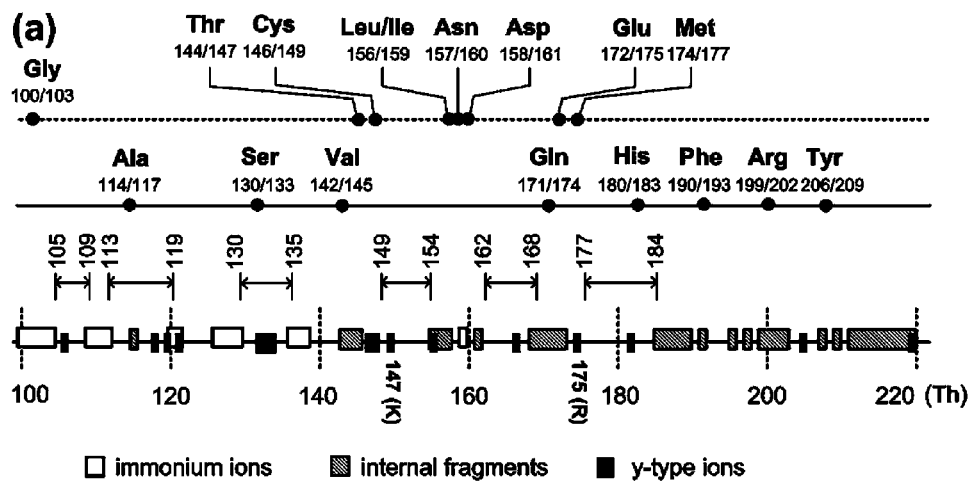
FIG. 2 is a schematic diagram showing a type of amino acid side chains available as a mass-tunable group ($R_T$) for MBIT strategy, in which (a) shows the amino acid side chains available as a mass-tunable group ($R_T$) for MBIT strategy and pairs of quantitation signal mass in case of using the same amino acid, with distribution of possible fragment ions having mass range of 220 Th or below in tandem mass spectra in case of mass spectrometry of peptides, and (b) shows eight different mass-tunable groups (used in the present invention) with no significant interference with possible low mass fragments at the mass range of 220 Th or below.

FIG. 2 is a schematic diagram showing a type of amino acid side chains available as a mass-tunable group ($R_T$) for MBIT strategy, in which (a) shows the amino acid side chains available as a mass-tunable group ($R_T$) for MBIT strategy and pairs of quantitation signal mass in case of using the same amino acid, with distribution of possible fragment ions having mass range of 220 Th or below in tandem mass spectra in case of mass spectrometry of peptides, and (b) shows eight different mass-tunable groups (used in the present invention) with no significant interference with possible low mass fragments at the mass range of 220Th or below.

The quantitation peak is shifted by changing the mass-tunable group ($R_T$), and as shown in FIG. 2, alanine(Ala), serine(Ser), histidine(His), valine(Val), glutamine(Gln), phenylalanine(Phe), arginine(Arg), and tyrosine(Tyr) side chains afford the signals at 114/117 Th, 130/133 Th, 180/183 Th, 142/145 Th, 171/174 Th, 190/193 Th, 199/202 Th, and 206/209 Th, respectively. The above described mass-tunable groups showed little overlap with other fragment ions generated during tandem mass spectrometry. In addition to the above described mass-tunable groups, as shown in FIG. 2, threonine(Thr), cysteine(Cys), leucine(Leu), isoleucine(Ile), asparagine(Asn), aspartic acid(Asp), glutamic acid(Glu), or methionine(Met) can be also used as a mass-tunable group. In the embodiment of the present invention, eight different amino acid side chains of alanine(Ala), serine(Ser), valine (Val), glutamine(Gln), histidine(His), phenylalanine(Phe), arginine(Arg), and tyrosine(Tyr) were used, as shown in FIG. 2b.

Figure 3:
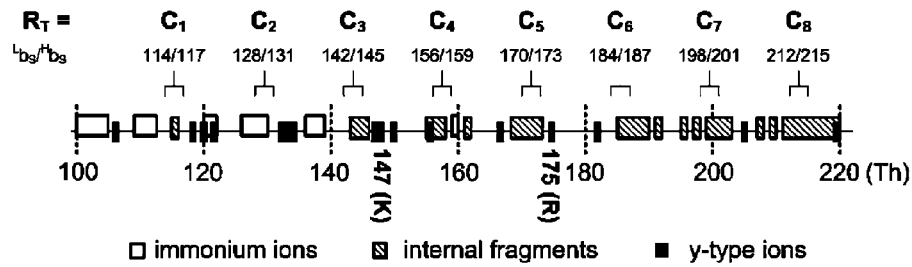
FIG. 3 is a diagram showing the quantitation signal of MBIT in case of using alkyl groups as a mass-tunable group ($R_T$) for MBIT strategy, in which (a) shows possible low mass fragments at the mass range of 220 Th or below in tandem mass spectra, and (b) shows the intrinsic tagging signature and quantitation signal mass of each MBIT, depending on the type of alkyl group that is used as a mass-tunable group.

FIG. 3 is a diagram showing the quantitation signal of MBIT having alkyl groups as a mass-tunable group ($R_T$) for MBIT strategy, in which (a) shows possible low mass fragments at the mass range of 220 Th or below in tandem mass spectra, and (b) shows the intrinsic tagging signature and quantitation signal mass of each MBIT, depending on the type of alkyl group that is used as a mass-tunable group.

The quantitation signal ($b_S$) is shifted by changing the mass-tunable group ($R_T$), and as shown in FIG. 3, methyl ($C_1$), ethyl ($C_2$), straight or branched chain propyl ($C_3$), straight or branched chain butyl ($C_4$), straight or branched chain pentyl ($C_5$), straight or branched chain hexyl ($C_6$), straight or branched chain heptyl ($C_7$), and straight or branched chain octyl ($C_8$) afford the signals at 114/117 Th, 128/131 Th, 142/145 Th, 156/159 Th, 170/173 Th, 184/187 Th, 198/201 Th, and 212/215 Th, respectively. When the mass-tunable group is methyl, ethyl, straight or branched chain propyl, straight or branched chain butyl, straight or branched chain pentyl, straight or branched chain hexyl, straight or branched chain heptyl, and straight or branched chain octyl, their $a_S$ ions deduced from the neutral CO-loss of $b_S$ are detected at 86/89 Th, 100/103 Th, 114/117 Th, 128/131 Th, 142/145 Th, 156/159 Th, 170/173 Th, and 184/187 Th, respectively. When the mass-tunable group is methyl, ethyl, straight or branched chain propyl, straight or branched chain butyl, straight or branched chain pentyl, straight or branched chain hexyl, straight or branched chain heptyl, and straight or branched chain octyl, the intrinsic tagging signature ($b_0$) ions of each MBIT appear at 188 Th, 202 Th, 216 Th, 230 Th, 244 Th, 258 Th, 272 Th, and 286 Th, respectively.

In an aspect of the present invention, the present invention relates to a compound represented by the following Formula 2 and the compound-linked analyte.

[Formula 2]

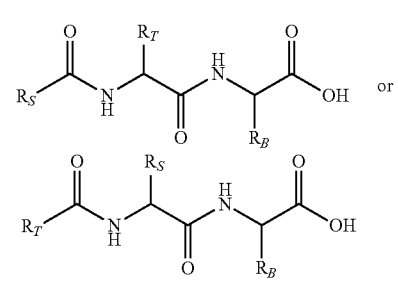

wherein $R_S$ and $R_B$ are straight or branched chain $C_1$-$C_{18}$ alkyl having one or more deuterium atoms, and $R_T$ is a mass-tunable group. In the present invention, the $R_S$ and $R_B$ are alkyl having the same number of carbon atoms, but different number of deuterium atoms. In the embodiment of the present invention, if $R_S$ is $CH_3$, $R_B$ is $CD_3$, or if $R_B$ is $CH_3$, $R_S$ is $CD_3$.

In the embodiment of the present invention, for the sake of convenience, the mass-tunable group $R_T$ may be selected from the group consisting of natural or artificial amino acid side chains having the same or similar property. The compound represented by Formula 2 can be converted to the compound of Formula 1 with the use of a proper activating reagent. Examples of the activating reagent may include a combination of N-hydroxysuccinimide(NHS)/1-ethyl-3-(3-dimethylaminopropyl)carbodiimide (EDC), a combination of 1-benzotriazol(HOBt)/N,N'-diisopropylcarboimide (DIC), (benzotriazol-1-yloxyl)tris (dimethylamino)phosphonium hexafluorophosphate(BOP), and a combination of NHS/EDC was used in the embodiment of the present invention.

Figure 4:
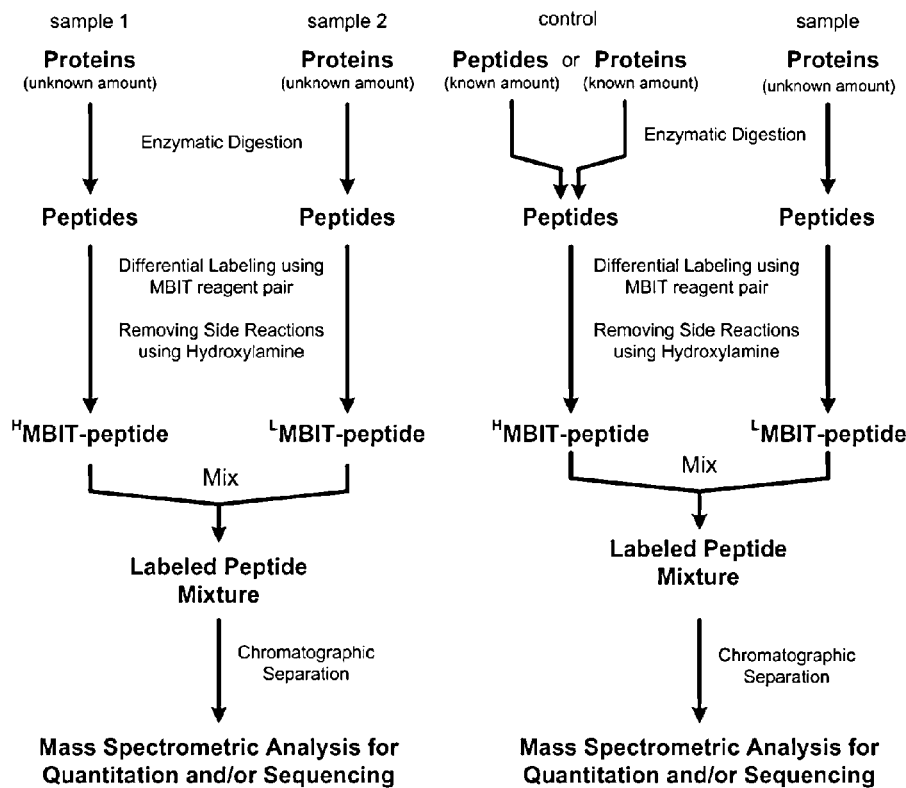
FIG. 4 is a diagram showing experimental procedures for relative and absolute quantitation of protein performed by using MBIT, in which (a) shows an experimental procedure for relative quantitation of the unknown amount of the same protein produced under the different conditions, and (b) shows an experimental procedure for absolute quantitation of the unknown amount of the identified protein.

FIG. 4 is a diagram showing experimental procedures for relative and absolute quantitation of protein performed by using MBIT, in which (a) shows an experimental procedure for relative quantitation of the unknown amount of the same protein produced under the different conditions, and (b) shows an experimental procedure for absolute quantitation of the unknown amount of the identified protein.

The MBIT compound is utilized for simultaneous peptide sequencing and protein quantification, as described in FIG. 4. The MBIT compound can be employed in both relative and absolute quantitation of protein, as shown in FIGS. 4(a) and 4(b).

The 2-plex relative quantitation is performed by the procedure as shown in FIG. 4(a). The proteins of two samples (unknown amount) are subjected to enzymatic digestion, respectively. The peptides from Sample 1 and the peptides from Sample 2 are labeled with $^H$MBIT and $^L$MBIT, respectively. Subsequently, they are mixed and separated by chromatography, followed by tandem mass spectrometry for simultaneous peptide sequencing and protein quantitation.

As shown in FIG. 4(b), the absolute quantitation can be accomplished, when peptides or proteins of known amounts are used to perform the procedures as in the above relative quantitation.

Figure 5A:
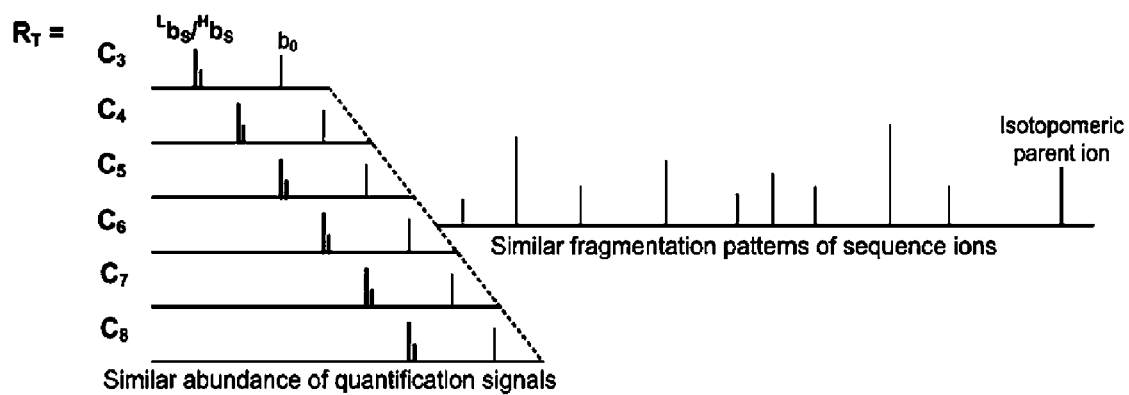
FIG. 5 is a diagram showing the tandem mass spectra of the set of MBITs having the same property but differential signal mass, and showing the simultaneous multiplexed quantification methods for three or more samples using two or more sets of MBITs.
Figure 5B:
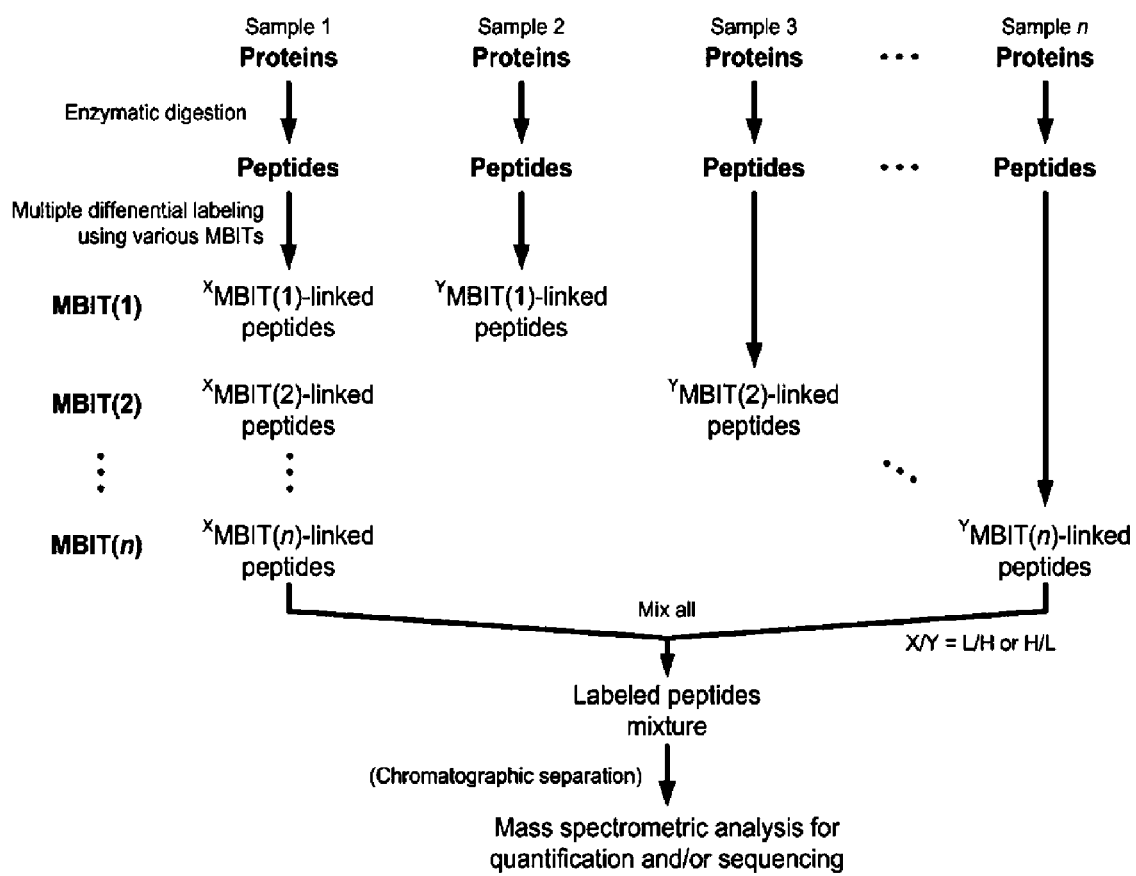
Figure 5C:
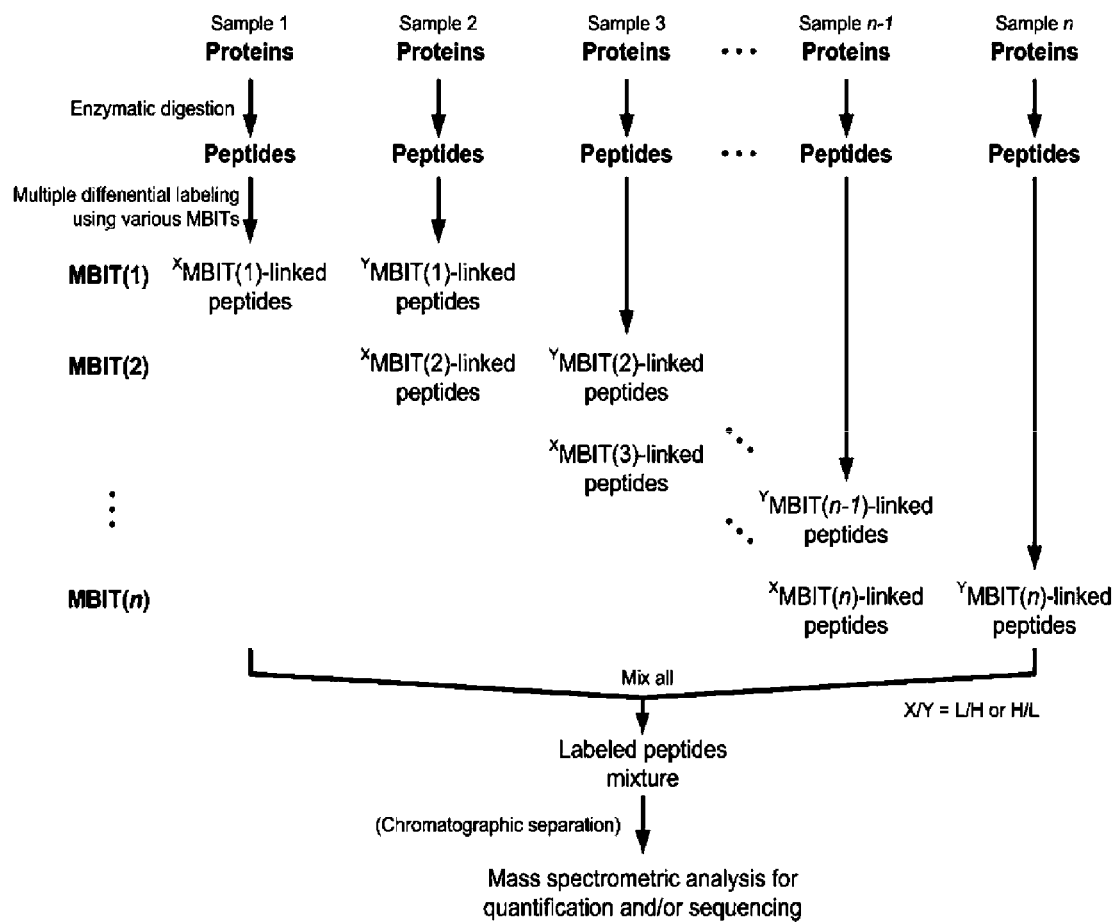

FIG. 5 is a diagram showing the tandem mass spectra of the set of MBITs having the same property but differential signal mass, and showing the simultaneous multiplexed quantification methods for three or more samples using two or more sets of MBITs.

The set of MBITs show differential quantitation signal mass but similar quantitation signal intensity by tuning the property of mass-tunable group, allowing the multiplexed quantification.

First, for multiplexed quantification, the protein samples produced under different conditions and environments are subjected to enzymatic digestion to prepare peptides. The first multiplexed quantification is performed as follows. Of the prepared peptides, aliquots of one digested peptide that is obtained under one condition are prepared in the same number of comparative samples, and each of them is linked with $^H$MBIT (or $^L$MBIT) variable mass labeling reagents having differential signal mass. The comparative peptides are linked with $^L$MBIT (or $^H$MBIT) variable mass labeling reagents having differential signal mass.

The second multiplexed quantification is performed as follows. Each prepared peptide are divided into two aliquots, and mixed with either $^H$MBIT(n−1) and $^L$MBIT(n) or $^L$MBIT(n−1) and $^H$MBIT(n). All of the labeled peptides are mixed and separated by chromatography. The isobaric parent ions of each labeled peptide are analyzed for sequencing and quantitation by tandem mass spectrometry, allowing the multiplexed quantification.

With regard to the first multiplexed quantification method, the result accuracy can be improved by statistical combinations of the analysis results, which are obtained by repeating the analysis with various MBITs for each comparative sample or by selecting a sample under different conditions as a control. The second multiplexed quantification method is advantageous over the first method, in the case where the relative amount is not easily analyzed by one process, because of a large difference in relative amounts.

Mode For The Invention

Hereinafter, the variable mass labeling reagentsand analysis methods for simultaneous peptide sequencing and protein quantitation using the same according to the present invention will be described in detail with reference to examples and the accompanying drawings. However, the present invention should not be construed as being limited to examples set forth herein, and it will be apparent to those skilled in the art that various modifications and changes may be made thereto without departing from the scope and spirit of the invention.

The following experiments were separately carried out, concerning that the mass-tunable group is alanine (Ala), serine (Ser), histidine (His), valine (Val), glutamine (Gln), phenylalanine (Phe), arginine (Arg), or tyrosine (Tyr) side chains, and the mass-tunable group is ethyl ($C_2$), propyl ($C_3$), butyl ($C_4$), pentyl ($C_5$), hexyl ($C_6$), heptyl ($C_7$), or octyl ($C_8$).

MBIT having the mass-tunable group of ethyl ($C_2$), propyl ($C_3$), butyl ($C_4$), pentyl ($C_5$), hexyl ($C_6$), heptyl ($C_7$), or octyl ($C_s$) has a dipeptide structure, conveniently expressed by $^H$X$_n$-Ala or $^L$X$_n$-Ala (H: heavy and L: light).

1. Synthesis of an Acid Form of MBITs

An acid form of MBIT reagents ($^X$MBIT-OH, X=L or H) was synthesized by the standard solid-phase peptide synthesis or solution-phase organic synthesis. The standard solid-phase peptide synthesis can be used for the preparation of all types of MBITs, where the mass-tunable group is an amino acid side chain and the corresponding mass-tunable group is a natural amino acid side chain such as alanine(Ala), serine (Ser), histidine(His), valine(Val), glutamine(Gln), phenylalanine(Phe), arginine(Arg), and tyrosine (Tyr), or the mass-tunable group is an N-acyl group or amino acid side chain and the corresponding mass-tunable group is ethyl ($C_2$), propyl ($C_3$), butyl ($C_4$), pentyl ($C_5$), hexyl ($C_6$), heptyl ($C_7$), or octyl ($C_8$). The solution-phase organic synthesis can be used for the preparation of the acid form of MBIT reagents, where the mass-tunable group is an amino acid side chain, and the corresponding mass-tunable group is hexyl ($C_6$), heptyl ($C_7$), or octyl ($C_8$).

FIG. 6 is a schematic diagram showing the process of synthesis of N-acylateddipeptide MBIT reagents using (a) the solid-phase synthesis and (b) the solution-phase synthesis.

(a) Solid-Phase Peptide Synthesis

Materials

Anhydrous N,N-dimethylformamide (DMF), piperidine, dichloromethane (DCM, HPLC grade), trifluoroacetic acid (TFA, HPLC grade), thioanisol (TA, >99.5%), ethanedithiol (EDT, >99.5%), anhydrous acetic acid, propionic acid, butyric acid, pentanoic acid, hexanoic acid, heptanoic acid, octanoic acid, nonanoic acid, and N-Fmoc-alanine were purchased from Sigma-Aldrich (St. Louis, Mo.). Acetic acid-d$_3$ and N-Fmoc-alanine-3,3,3-d$_3$ are purchased from CDN isotope (Toronto, Canada). 2-Clorotrityl resin was purchased from Merck. N,N'-diisopropylcarboimide (DIC), 1-benzotriazol, and other N-Fmoc-protected amino acids were purchased from Advanced ChemTech (Louisville, Ky.).

Synthesis

1) Step 1

N-Fmoc-alanine or N-Fmoc-alanine-3,3,3-$d_3$ (75 mg) was dissolved in dehydrated DCM solution (1 mL), and completely dissolved by addition of DMF (100 μL). The prepared N-Fmoc amino acid solution and DIPEA (170 μL) were mixed with 2-chlorotrityl resin (0.1 g) contained in a flame-dried vial, and the mixture was mildly stirred for 2-4 hrs. The resin was added to a polypropylene cartridge adapted for peptide synthesis (total volume: 5 mL), and rinsed with a mixed solution of DCM/methanol/DIPEA (17/2/1, v/v/v) three times. Thereafter, the resin was washed with DCM three times, and washed with DMF twice. Then, the resin was additionally washed with DCM twice, the solution was removed therefrom, and completely dried under reduced pressure.

2) Step 2

Approximately 3 mL of DMF was added to the dried resin that was prepared in Step 1, and stirred for 2-3 min. The process of removal of DMF was repeated five times, and the resin was sufficiently soaked in DMF. A 25% piperidine solution (about 3 mL) in DMF was added to the resin, and stirred for 5 min to remove the solution. Then, the 25% piperidine solution (about 3 mL) was additionally added to the resin, and stirred for 15 min to remove the solution. Subsequently, the resin was washed with DMF three times, with methanol three times, and with DMF three times.

3) Step 3

The MBIT reagent having a mass-tunable group of amino acid side chain was synthesized as follows.

N-Fmoc-amino acid (0.6 M, 1 mL) (one of alanine, serine, valine, glutamine, histidine, phenylalanine, arginine, and tyrosine) in DMF was added to the resin prepared in Step 2. Each 1 mL of 0.6 M 1-benzotriazol and DIC in DMF was added thereto, and stirred for 2 hrs and 30 min. After removing the mixed solution, the resin was sufficiently washed with DMF three times, with methanol three times, and with DMF three times.

The MBIT reagent having a mass-tunable group of acyl group was synthesized as follows.

Each 1 mL of 0.6 M N-Fmoc-alanine-$d_0$ (or N-Fmoc-alanine-3,3,3-$d_3$), 1-benzotriazol, and DIC in DMF was added to the alanine-$d_3$(or alanine-$d_0$)-conjugated resin prepared in Step 2, and slowly stirred for 2 hrs and 30 min. After removing the mixed solution, the resin was sufficiently washed with DMF three times, with methanol three times, and with DMF three times.

4) Step 4

Approximately 3 mL of 25% piperidine in DMF was added to the resin prepared in Step 3, and stirred for 5 min. After removing the solution, 25% piperidine solution (3 mL) in DMF was added to the resin, and stirred for 15 min. Then, the resin was sufficiently washed with DMF three times, with methanol three times, and with DMF three times.

5) Step 5

The MBIT reagent having a mass-tunable group of amino acid side chain was synthesized as follows.

Acetic acid-$d_0$ or acetic acid-$d_3$ (0.6 M, 1 mL) in DMF was added to the resin prepared in Step 4. If the resin was treated with N-Fmoc-alanine-$d_0$, acetic acid-$d_3$ was used. If the resin was treated with N-Fmoc-alanine-3,3,3-$d_3$, acetic acid-$d_0$ was used. In addition, each 1 mL of 0.6 M 1-benzotriazol and DIC in DMF was added to the resin, and slowly stirred for 2 hrs and 30 min. After removing the mixed solution, the resin was sufficiently washed with DMF three times, with methanol three times, with DMF three times, and with methanol three times. Subsequently, the resin was completely dried under reduced pressure, and transferred to a vial.

The MBIT reagent having a mass-tunable group of N-acyl group was synthesized as follows.

Each 1 mL of 0.6 M carboxylic acid (propionic acid, butyric acid, pentanoic acid, hexanoic acid, heptanoic acid, octanoic acid, or nonanoic acid), 1-benzotriazol, and DIC in DMF was added to the resin prepared in Step 4, and slowly stirred for 2 hrs and 30 min. After removing the mixed solution, the resin was sufficiently washed with DMF three times, with methanol three times, with DMF three times, and with methanol three times. Subsequently, the resin was completely dried under reduced pressure, and transferred to a vial.

6) Step 6

A mixed solution (2 mL) of TFA/benzene/TA/distilled water/EDT (16.5/1/1/1/0.5, v/v/v/v) was added to the resin prepared in Step 5, and stirred for 3 hrs. During the process, the synthesized acid form of MBIT reagent was cleaved from the resin. The resin was filtered out, and the remaining solution was collected and dried to a volume of 200 μL or less by nitrogen. Cold ether was added to the solution to precipitate a white powder (an acid form of MBIT reagent). The precipitated product was washed with cold ether three or four times, and completely dried under reduced pressure.

(b) Solution-Phase Organic Synthesis

Materials 2-amino-4-pentenoic acid, anhydrous acetic acid ($Ac_2O$-$d_0$), Boc-1-alanine-$d_0$, TFA, 4-octene, 5-decene, 1-heptene, and Grubbs's catalyst (2nd generation) were purchased from Sigma-Aldrich (St. Louis, Mo.), and per-deuteratedanhydrous acetic acid ($Ac_2O$-$d_6$) were purchased from CDN Isotopes (Quebec, Canada).

Synthesis

1) Step 1

2-Amino-4-pentenoic acid (2 mmol) was dissolved in water (pH 9-10, 4 mL), and anhydrous acetic acid-$d_0$ or anhydrous acetic acid-$d_3$ (4.0 mmol) was added thereto at 0° C. 8 M NaOH was added thereto, and its pH was adjusted to 10. The reaction mixture was stirred at 0° C. for 4 hrs. A concentrated hydrochloric acid solution was added to the solution to adjust the pH to 2 or less. The resultant was dissolved in methanol, purified and dried to recover solid 2-acetamido-4-pentenoic acid.

2) Step 2

Benzyl bromide was added to N-Boc-protected alanine to give N-Boc-alanine benzyl ester, and then Boc was removed by addition of TFA to prepare alanine benzyl ester. 1.5 mL of 1 M NaOH and di-tertiary-butyl bicarbonate (1.1 mmol) were added to 0.33 M 1-alanine-$d_3$(1 mmol) in a mixture of dioxane and water (2/1, v/v), and then stirred at room temperature for 6 hrs. After evaporating dioxane, the mixture was cooled with ice, and a saturated solution of $KHSO_4$ was added to the mixture to adjust the pH to 2-3. The organic product was extracted using 10 mL of ethyl acetate (EA) three times, and dried over anhydrous $Na_2SO_4$. The resultant was purified by silica gel chromatography to give N-Boc-dl-alanine-$d_3$ (0.14 g, 0.74 mmol). 0.5 mmol of N-Boc-dl-alanine-$d_0$ or N-Boc-dl-alanine-$d_3$ was dissolved in anhydrous acetone (5 mL), and potassium carbonate (0.75 mmol) and benzyl bromide (0.55 mmol) were added thereto. After refluxing for 5 hrs, the reaction product was cooled to room temperature, concentrated, and then dissolved in chloroform (10 mL). The organic layer was washed with a concentrated aqueous solution of sodium carbonate (30 mL), and dried over $Na_2SO_4$, followed by silica gel chromatography to give the white solid N-Boc-dl-alanine-$d_0$ benzyl ester or N-Boc-dl-alanine-$d_3$ benzyl ester. N-Boc-dl-alanine-$d_0$ benzyl ester or N-Boc-dl-alanined$_3$ benzyl ester (0.98 mmol) was dissolved in DCM(10 mL), 8 mmol TFA was added thereto at 0° C., and stirred for 1 hr. The solvent was removed under reduced pressure, and the residue was dried under high vacuum. The oily product (alanine-d$_0$ benzyl ester or alanine-d$_3$-benzyl ester) was stored in anhydrous THF (2 mL).

3) Step 3

A BOP reagent (1.01 mmol) was added to alanine-d$_0$ benzyl ester or alanine-d$_3$-benzyl ester (0.55 mmol) in THF (5 mL), prepared in Step 2, and stirred at room temperature for 30 min. DIPEA (3.36 mmol) was added thereto at 0° C., and stirred at room temperature for 15 min. Then, 2-acet-d$_3$-amido-4-pentenoic acid or 2-acet-d$_0$-amido-4-pentenoic acid in anhydrous THF, prepared in Step 1 was added thereto, and then stirred at room temperature overnight. After evaporating the solvent, the residue was dissolved in EA. The organic layer was washed with water. The residual oily product was purified by silica gel flash chromatography to give colorless solid, benzyl 2-(2-acetamido-4-penteneamido)propanate.

4) Step 4

Benzyl 2-(2-acetamido-4-penteneamido)propanate prepared in Step 3, alkene (4-octene, 5-decene, or 1-heptene), and Grubbs's catalyst were added to DCM, and refluxed at 40° C. for 24 hrs. After removing the catalyst and solvent, the resultant was purified by silica gel chromatography. The reaction product was mixed with 20 mol % Pd(OH)$_2$ in anhydrous methanol, and then stirred under H$_2$ pressure of 1 atm at room temperature overnight. After filtering out the catalyst, the resultant was concentrated under vacuum, followed by recrystallization using a mixture of methanol and ether (1:1, v/v) to give an acid form of MBIT reagent.

2. Coupling of MBIT Reagent with Target Peptide

Materials

Anhydrous acetonitrile (ACN, HPLC grade), anhydrous DMF, hydroxylamine hydrochloride, trifluoroacetic acid (TFA, HPLC grade), alpha-cyano-4-hydroxycinnamic acid (HCCA), and N-hydroxysuccinimide (NHS) were purchased from Sigma-Aldrich (St. Louis, Mo.). 1-Ethyl-3-(3-dimethylaminopropyl)carbodiimide(EDC) was purchased from Pierce (Rockford, Ill.). Bovine serum albumin (BSA) was purchased from Calbiochem (San Diego, Calif.).

Preparation of Active Ester of MBIT Reagent and Coupling with Model Reptide

Figure 7:
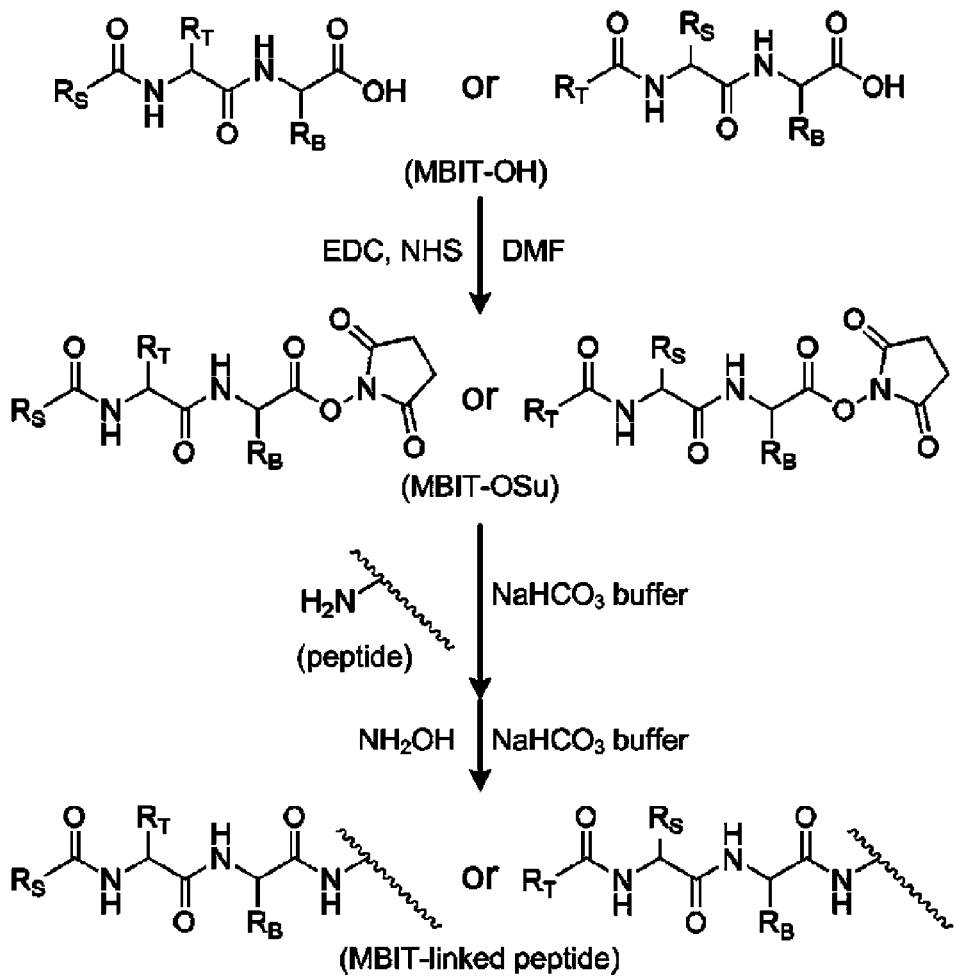
FIG. 7 is a schematic diagram showing experimental method for the formation of active ester of the MBIT reagent and coupling of the formed active esters of MBIT with target peptides.

FIG. 7 is a schematic diagram showing experimental method for the formation of active ester of the MBIT reagent and coupling of the formed active esters of MBIT with target peptides.

The preparation method of succinimidyl ester (OSu) of MBIT reagent and coupling with model peptides are depicted in FIG. 7. $^X$MBIT-OH(X=L or H), EDC, and NHS were dissolved in DMF to a final concentration of 60, 35, 40 mM, respectively, and stirred at room temperature for 45 min. The prepared $^X$MBIT-OSu solution was used for coupling with an analyte without additional purification.

Angiotensin II (DRVYIHPF) (SEQ ID NO:2) or leucine enkephalin (YGGFL) (SEQ ID NO:3) was used as a model peptide. When the experiment was performed using N-acetylated dipeptide MBIT reagents having the mass-tunable group of a natural amino acid side chain such as alanine(Ala), serine(Ser), histidine(His), valine(Val), glutamine(Gln), phenylalanine(Phe), arginine(Arg), or tyrosine(Tyr), a model peptide mixture of angiotensin II and leucine enkephalin (molar ratio of 1:1) was used. When the experiment was performed using MBIT reagents having the mass-tunable group of ethyl (C$_2$), propyl (C$_3$), butyl (C$_4$), pentyl (C$_5$), hexyl (C$_6$), heptyl (C$_7$), or octyl (C$_8$), angiotensin II was only used as a model peptide.

The model peptide or peptide mixture was dissolved in 50 mM sodium bicarbonate (NaHCO$_3$) buffer to a concentration of 0.4 mM. 10 μL of the model peptide solution was mixed with 10 μL of the prepared $^L$MBIT-OSu or $^H$MBIT-OSu solution, and stirred at room temperature for 5 hrs. Then, 10 μL of hydroxylamine solution (80 mM in 100 mM NaHCO$_3$) was added thereto, and stirred for 5 hrs or longer to reverse side reactions and to inactivate excess MBIT-OSu reagents. The reaction was terminated with 5 μl of 10% TFA.

Conjugation of MBITs to Tryptic Peptides of BSA

MBIT reagents having the mass-tunable group of a natural amino acid side chain such as alanine(Ala), serine(Ser), histidine(His), valine(Val), glutamine(Gln), phenylalanine(Phe), arginine(Arg), or tyrosine(Tyr) was used to perform the conjugation to tryptic peptides of BSA.

BSA dissolved in 100 mM sodium bicarbonate buffer (pH 8.1) (0.6 mg/mL) was mixed with modified trypsin dissolved in 0.1% acetic acid (0.1 μg/μL) at a weight ratio of 60:1 and incubated at 38° C. for 12 hrs. Tryptic peptides were divided into two aliquots of 16 μL and mixed with either $^H$MBIT-OSu or $^L$MBIT-OSu solution (14 μL), and stirred for 30 min. Additionally, 6 μL of $^H$MBIT-OSu or $^L$MBIT-OSu solution was added, and stirred for 30 min-2 hrs. Then, 10 μL of 100 mM hydroxylamine was added, and stirred for 4 hrs or longer to reverse side reactions. The residual $^X$MBIT-Osu was removed. The reaction was terminated with 10 μL of 10% TFA.

Conjugation of MBITs to Tryptic Peptides of Hsc82p

MBIT reagents having a mass-tunable group (R$_T$=C$_n$) of hexyl (C$_6$), heptyl (C$_7$), or octyl (C$_8$) were used to perform the conjugation to tryptic peptides of Hsc82.

An N-terminal hemagglutinin (HA)-tagged Hsc82 protein was obtained from four-physiological states. HA-Hsc82 protein expression conditions were divided into four groups by combinations of the presence of Hsp82 protein that is one of the Hsp90 family together with Hsc82 and yeast growth temperature, as shown in FIG. 22(a). The norm 30 represents that yeast having both Hsp82 and Hsc82 proteins was cultured at 30° C., the norm 39 represents that yeast having both Hsp82 and Hsc82 proteins was cultured at 39° C. for heat induction, the del 30 represents that yeast deficient for Hsp82 protein was cultured at 30° C., and the del 39 represents that yeast deficient for Hsp82 protein was cultured at 39° C. for heat induction. HA-Hsc82 proteins expressed under the conditions were isolated from cell lysates, purified using anti-HA matrix (clone 3F10, Roche), and separated by SDS-polyacrylamide gel. The expressed HA-Hsc82 proteins were visualized by Sypro Ruby staining (Molecular Probes, Eugene, Oreg.), and quantified using a VersaDoc 5000 MP gel imaging system (Bio-Rad, Hercules, Calif.).

To obtain Hsc82 peptides, each sample was digested with trypsin as follows. Protein bands were excised from the gel and incubated in 100 mM NaHCO$_3$ buffer for 20 min. After removing the buffer, the gels were cut into small pieces, and ACN was added thereto to remove water. 0.66 μg of trypsin in 50 mM NaHCO$_3$ buffer was added to each sample, and incubated at 37° C. for 20 hrs. Tryptic peptides were extracted by swelling gel pieces with a mixed solution of distilled water and ACN, and dried.

Distilled water (35 μL) was added to each dried sample. Aliquots (4 μL) from each sample solution were mixed with $^H$MBIT-OSu or $^L$MBIT-OSu solution (4 μL), and stirred for 5 hrs. At this time, norm 39 and $^L$X$_6$-Ala, del 30 and $^L$X$_7$-Ala, del 39 and $^L$X$_8$-Ala, norm 30 and $^H$X$_6$-Ala, $^H$X$_7$-Ala, and $^H$X$_8$-Ala were reacted with each other. Then, hydroxylamine solution (80 mM, 4 μL) was added, and stirred for 5 hrs or longer to reverse side reactions and to inactivate excess MBIT-OSu reagents. The reaction was terminated with 2 μl of 10% TFA.

MALDI Sample Preparation of MBIT-Model Peptide

A solution of $^X$MBIT-linked model peptide was diluted 500 times in 0.1% TFA for MALDI analysis. $^L$MBIT and $^H$MBIT-model peptides were mixed in seven different ratios ([L]/[H] =1/1, 2.3/1, 4/1, 6.3/1, 9/1, 12.3/1, 16/1). Each sample was mixed with a matrix solution (5 mg/mL HCCA in 50/50/ 0.1H$_2$O/ACN/TFA) in a volume ratio of 1:1. The sample/ matrix mixture (1 μL) was loaded on a MALDI target plate. The total amount of model peptides, angiotensin II and leucine enkephalin, per spot was 250 fmol.

LC-MALDI Sample Preparation of MBIT-Linked Tryptic Peptides of BSA and Hsc82p $^H$MBIT or $^L$MBIT-linked tryptic peptides were mixed in a ratio of 1:1, and an aliquot (6.4 μL) was injected into a Reverse-Phase Nano-Liquid Chromatography (RP-nano-LC) system (LC Packings, Sunnyvale, Calif.) equipped with a PepMap column (100-pore, 3-m particle diameter, 75-m i.d., 150-mm length). LC was run for 60 min with the flow rate of 0.3 μL/min using a two solvent gradient: H$_2$O/ACN/ TFA=95/5/0.1 (solvent A) and ACN/TFA=100/0.1 (solvent B). The [A]/[B] gradient was started from 100/0, changed to 30/70 between 0 and 20 min and to 0/100 for 20~40 min, maintained at 0/100 between 40 and 45 min, and immediately dropped at 45 min and kept at 100/0 between 45 and 60 min. The eluted peptides were collected in every 25 sec on a single MALDI spot with a matrix solution using a Probot microfraction collector (Dionex, Sunnyvale, Calif.). Each sample was eluted over total 144 MALDI spots in 60 min.

MALDI-MS and MS/MS

To analyze the samples applied to the MALDI targets, a 4700 Proteomics-Analyzer(Applied Biosystems, Foster City, Calif.) was employed in a positive mode at the mass range of 500-2500 Th. At each MALDI spot, the time-of-flight(TOF) mass spectra were obtained by accumulating 1000 single laser-shot spectra.

$^X$MBIT-linked model peptide ions were detected at different m/z values according to the mass-tunable group R$_T$, and $^X$MBIT-linked model peptides were selected as parent ions for tandem mass spectrometry. $^X$MBIT-linked tryptic peptides of BSA were detected at different elution time.

For tandem mass spectrometry, CID was performed under 1.3×10$^{-6}$ ton of air. The CID spectra were obtained by summing 2000 single laser-shot spectra. The baseline of the CID mass spectra was corrected using ABI-4700 DataExplore software (Applied Biosystems, Foster City, Calif.). After baseline correction, the heights of $^L$b$_S$ and $^H$b$_S$ ions were used for relative quantitation. Each CID spectrum was analyzed using PEAKS 4.5 (Bioinformatics Solutions Inc., Canada) to perform de novo sequencing.

3. Experimental Results on MBIT (a) Mass-tunable group of natural amino acid residue, including alanine(Ala), serine(Ser), histidine (His), valine (Val), glutamine (Gln), phenylalanine (Phe), arginine(Arg), and tyrosine(Tyr)

Confirmation of N-acetylated Dipeptide MBITs

Figure 8A:
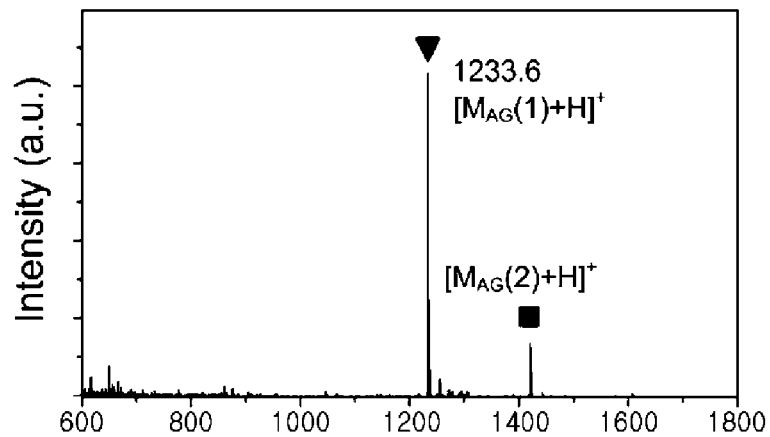
FIG. 8 is the results of MALDI mass spectrometry of peptide mixtures of angiotensin II and leucine enkephalin linked with eight pairs of N-acetylated dipeptide MBIT reagents [Ac-Xxx-Ala Xxx having a mass-tunable group is (a) alanine, (b) serine, (c) valine, (d) glutamine, (e) histidine, (f) phenylalanine, (g) arginine, and (h) tyrosine].
Figure 8B:
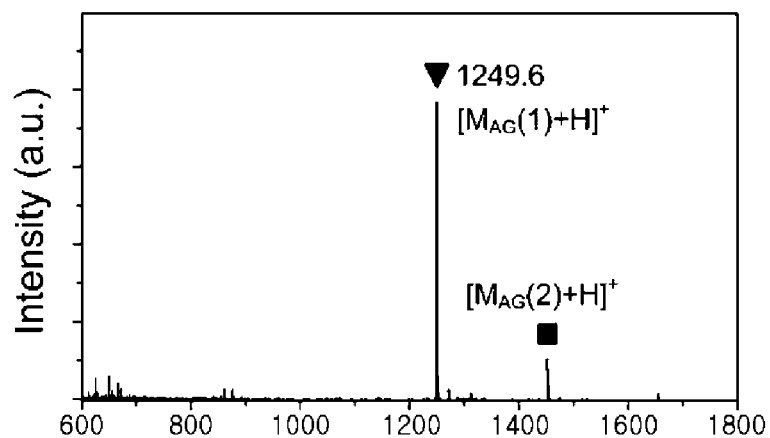
Figure 8C:
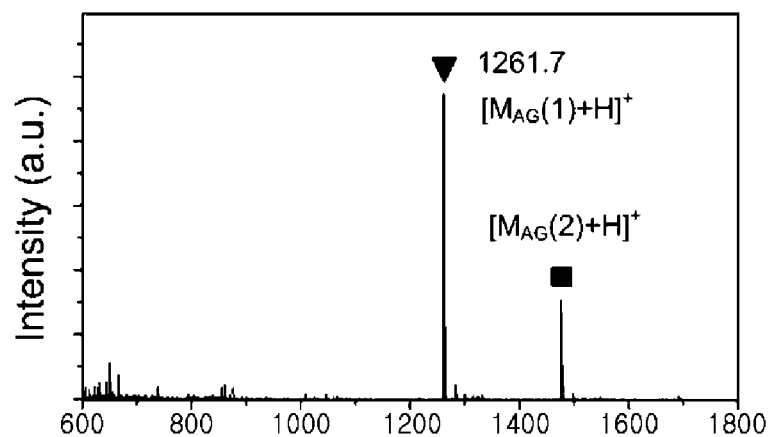
Figure 8D:
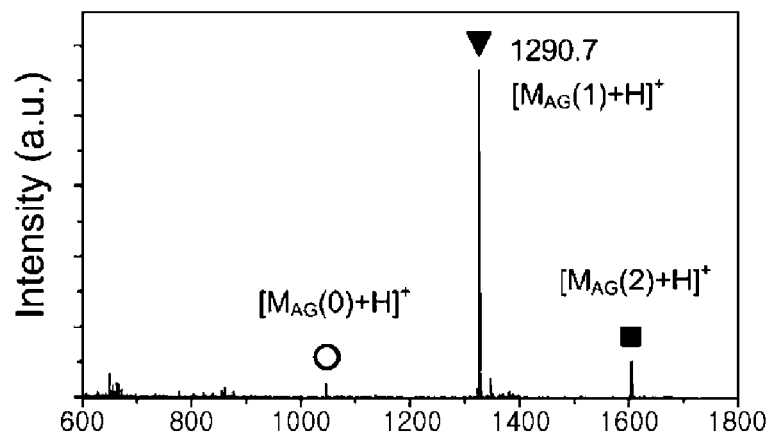
Figure 8E:
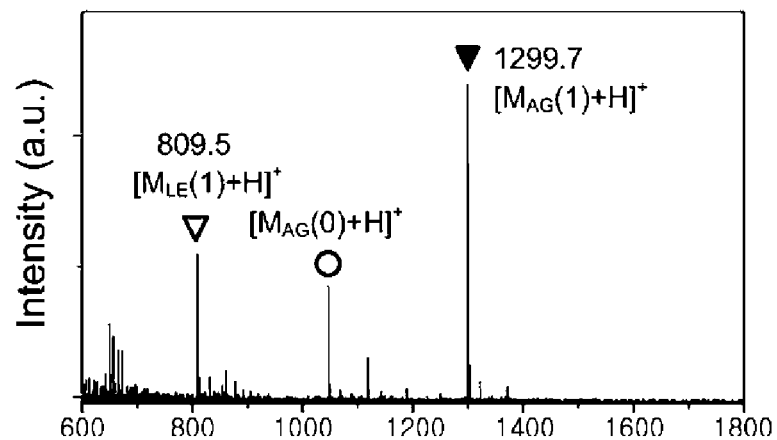
Figure 8F:
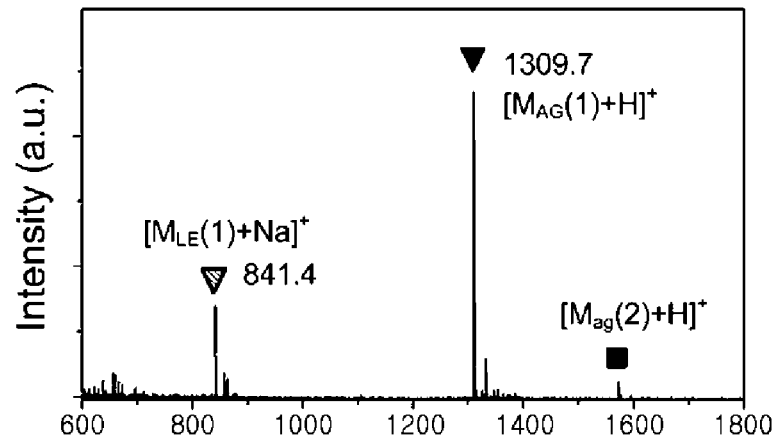
Figure 8G:
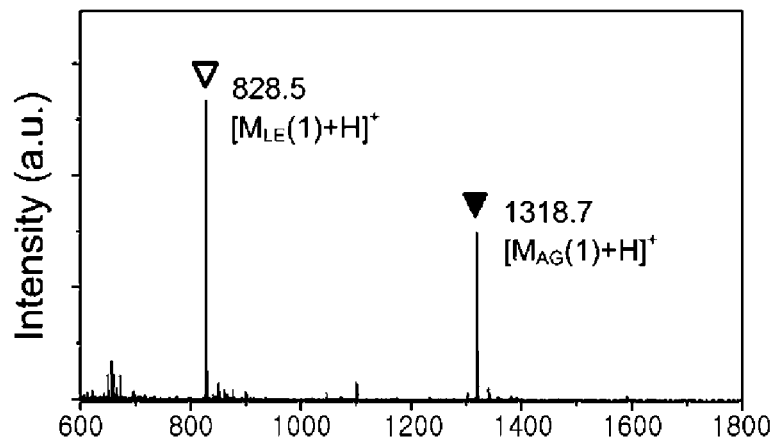
Figure 8H:
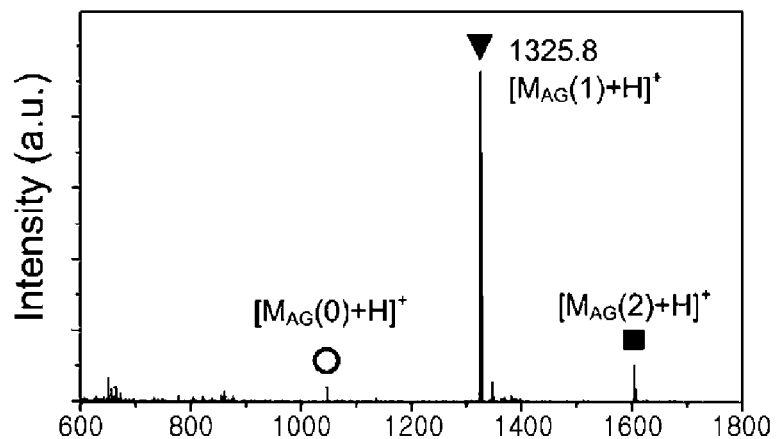
Figure 9:
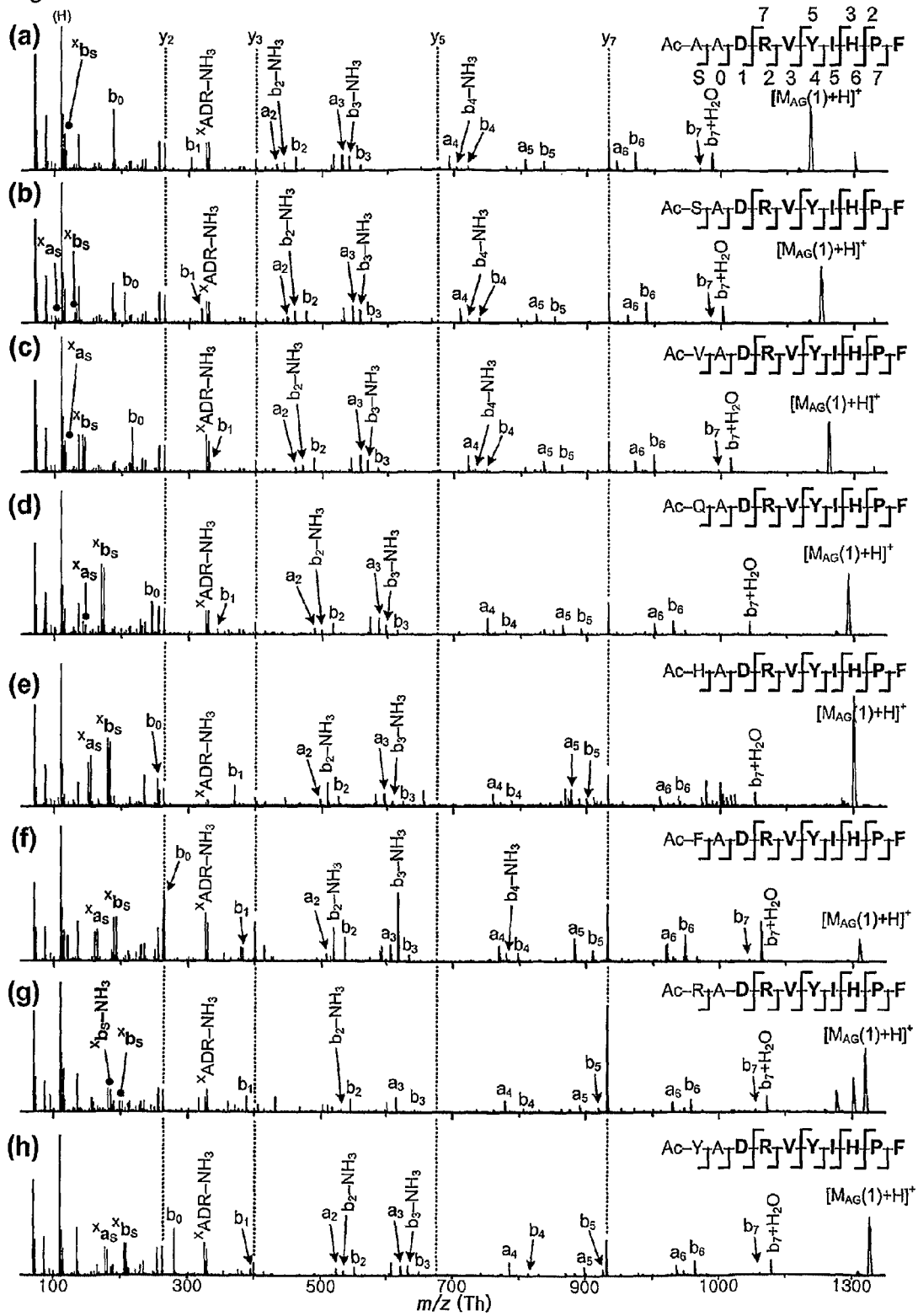
FIG. 9 is the results of MALDI tandem mass spectrometry of angiotensin II ($[M_{AG}(1)+H]^+$) each linked with eight different pairs of N-acetylated dipeptide MBIT reagents as described in FIG. 8 [Ac-Xxx-Ala Xxx having a mass-tunable group is (a) alanine, (b) serine, (c) valine, (d) glutamine, (e) histidine, (f) phenylalanine, (g) arginine, and (h) tyrosine].

In order to confirm N-acetylated dipeptide MBITs, angiotensin II (1045.5 Da) was labeled with each MBIT reagent to detect signal mass of [M$_{AG}$(1)+H]+ ion (FIG. 8), and to perform tandem mass spectrometry (FIG. 9). $^L$MBIT and $^H$MBIT-linked angiotensin II appeared at the same mass. When the mass-tunable group was alanine, serine, valine, glutamine, histidine, phenylalanine, arginine, and tyrosine side chains, [M$_{AG}$(1)+H]+ ions were detected at 1233.6 Th, 1249.6 Th, 1261.7 Th, 1290.7 Th, 1299.7 Th, 1309.7 Th, 1318.7 Th, and 1325.7 Th, respectively. When the mass-tunable group was alanine, serine, valine, glutamine, histidine, phenylalanine, arginine, and tyrosine side chains, the tagging signature and quantitation signal mass appeared at 188 Th (b$_0$), 114 Th ($^L$b$_S$), and 117 Th ($^H$b$_S$), 204 Th (b$_0$), 130 Th ($^L$b$_S$), and 133 Th ($^H$b$_S$), 216 Th (b$_0$), 142 Th (L b$_S$), and 145 Th ($^H$b$_S$), 245 Th (b$_0$), 171 Th ($^L$b$_S$), and 174 Th ($^H$b$_S$), 254 Th (b$_0$), 180 Th ($^L$b$_S$), and 183 Th ($^H$b$_S$), 264 Th (b$_0$), 190 Th ($^L$b$_S$), and 193 Th ($^H$b$_S$), 273 Th (b$_0$), 199 Th ($^L$b$_S$), and 202 Th ($^H$b$_S$), and 280 Th (b$_0$), 206 Th ($^L$b$_S$), and 209 Th ($^H$b$_S$), respectively. The results indicated that N-acetylated dipeptide MBIT reagents were favorably synthesized using natural amino acid side chains.

Tandem Mass Spectrometry of N-acetylated Dipeptide MBIT-linked Model Peptides

FIG. 8 is the results of MALDI mass spectrometry of peptide mixture of angiotensin II and leucine enkephalin linked with eight pairs of N-acetylated dipeptide MBIT reagents, in which (a-h) show MALDI-TOF mass spectra of model peptides linked with eight pairs of MBIT reagents having eight different mass-tunable groups R$_T$ shown in FIG. 2(b). As shown in FIG. 8, XX of [M$_{XX}$(n)+H]$^+$ represents the type of peptide (AG=angiotensin II, LE=leucine enkephalin), and n represents the number of MBIT reagent linked to peptide. In the N-acetylated dipeptide MBIT reagent (N-acetyl-Xxx-Ala, or Ac-XA), when Xxx (or X) having a mass-tunable group is (a) alanine, (b) serine, (c) valine, (d) glutamine, (e) histidine, (f) phenylalanine, (g) arginine, and (h) tyrosine, each MALDI-TOF spectrum is shown. When a mass-tunable group was alanine, serine, valine, glutamine, histidine, phenylalanine, arginine, and tyrosine, [M$_{AG}$(1)+H]$^+$ ions corresponding to angiotensin II were detected at 1233.6 Th, 1249.6 Th, 1261.7 Th, 1290.7 Th, 1299.7 Th, 1309.7 Th, 1318.7 Th, and 1325.7 Th, respectively. In addition, when a mass-tunable group was histidine and arginine, [M$_{LE}$(1)+H]$^+$ ions corresponding to leucine enkephalin were detected at 809.5 Th and 828.5 Th, respectively. The mass values increased by coupling each MBIT reagent with model peptide were identical to the theoretically expected mass values increased by each MBIT reagent, which indicated that each MBIT reagent was successfully synthesized.

Leucine enkephalin was detected only after labeling with MBITs having basic mass-tunable group (R$_T$). All of MBIT-linked angiotensin II ([M$_{AG}$(1)+H]$^+$) were detected in MALDI spectra, irrespective of the type of mass-tunable group R$_T$. [M$_{AG}$(2)+H]$^+$ suggesting that side reactions occurred in tyrosine side chain of angiotensin II was detected, but the intensity was weaker than that of [M$_{AG}$(1)+H]$^+$. As shown in FIG. 8(e), unreacted angiotensin II ([M$_{AG}$(0)+H]$^+$) was strongly detected only when the mass-tunable group R$_T$ was a histidine side chain (Ac-HA MBIT), which could be easily prevented by improving the purity of reagent during synthesis and purification process of Ac-HA MBIT. From the relative intensities shown in FIG. 8, it was inferred that except for Ac-HA MBIT, coupling of MBITs with peptides proceeded completely.

Unlike angiotensin II, leucine enkephalin has no basic amino acid in its peptide sequence, thus it is not easily detected in MALDI mass spectra. As shown in FIG. 8(e) and (g), however, when Ac-HA and Ac-RA MBITs having a basic mass-tunable group R$_T$ were linked to leucine enkephalin, strong signals were detected in MALDI mass spectra, which indicated that MBIT reagents having basic mass-tunable group increased the ionization yield of peptides that were not easily detected in the known MALDI mass spectra, so as to allow their detection in MALDI mass spectra.

FIG. 9 is the results of MALDI tandem mass spectrometry of angiotensin II ($[M_{AG}(1)+H]^+$) each linked with eight different pairs of N-acetylated dipeptide MBIT reagents, in which with respect to each pair of MBIT reagent, $^H$MBIT-linked peptide and $^L$MBIT-linked peptide were mixed in a mixing ratio of 1:1 to perform tandem mass spectrometry. In FIG. 9(a-h), CID spectra of angiotensin II linked with MBIT reagents having different amino acid residues are shown, in which each CID spectrum shows angiotensin II linked with Ac-AA, Ac-SA, Ac-VA, Ac-QA, Ac-HA, Ac-FA, Ac-RA, or Ac-YA MBIT, and each MBIT reagent has a [L]/[H] ratio of 1/1. Since MBIT reagent was linked to the N-terminal primary amine, y-type fragment ions were detected at the same m/z values, irrespective of the types of MBIT reagents. On the contrary, a- or b-type fragment ions were detected at the different m/z values, according to the type of mass-tunable group. Except for Ac-RA MBIT in FIG. 9(g), other seven-different MBITs displayed similar fragment ion distribution in CID spectra. It can be seen that Ac-RA MBIT has strong basic arginine side chain to affect the fragment ion distribution. The tagging signature ($b_0$) and quantitation signal mass $^X b_S$ ion pair (X=L or H) appeared at the different m/z values according to the type of MBITs. Ac-AA MBIT displayed the tagging signature ion and quantitation signal ion pair at 188 Th ($b_0$), 114 Th ($^L b_S$), 117 Th ($^H b_S$), Ac-SA MBIT at 204 Th ($b_0$), 130 Th ($^L b_S$), 133 Th ($^H b_S$), Ac-VA MBIT at 216 Th ($b_0$), 142 Th ($^L b_S$), 145 Th ($^H b_S$), Ac-QA MBIT at 245 Th ($b_0$), 171 Th ($^L b_S$), 174 Th ($^H b_S$), Ac-HA MBIT at 254 Th ($b_0$), 180 Th ($^L b_S$), 183 Th ($^H b_S$), Ac-FA MBIT at 264 Th ($b_0$), 190 Th ($^L b_S$), 193 Th ($^H b_S$), Ac-RA MBIT at 273 Th ($b_0$), 199 Th ($^L b_S$), 202 Th ($^H b_S$), and Ac-YA MBIT at 280 Th ($b_0$), 206 Th ($^L b_S$), 209 Th ($^H b_S$), which agreed with the values expected in FIG. 2(b), indicating successful synthesis of N-acetylated dipeptide MBIT reagents.

$^X b_S$ ion pair may be additionally dissociated by surplus energy during CID. As shown in FIG. 9, $^X b_S$-$NH_3$ deduced from the neutral $NH_3$-loss in arginine side chain of Ac-RA MBIT were detected at 182, 185 Th. Of other seven different MBITs, Ac-AA MBIT displayed their $^X a_S$ ions (28 Da loss) that were deduced from the neutral CO-loss of $^X b_S$ at 86 Th ($^L a_S$) and 89 Th ($^H a_S$), Ac-SA MBIT at 102 Th ($^L a_S$) and 105 Th ($^H a_S$), Ac-VA MBIT at 114 Th ($^L a_S$) and 117 Th ($^H a_S$), Ac-QA MBIT at 143 Th ($^L a_S$) and 146 Th ($^H a_S$), Ac-HA MBIT at 152 Th ($^L a_S$) and 155 Th ($^H a_S$), Ac-FA MBIT at 162 Th ($^L a_S$) and 165 Th ($^H a_S$), and Ac-YA MBIT at 178 Th ($^L a_S$) and 181 Th ($^H a_S$).

Figure 10:
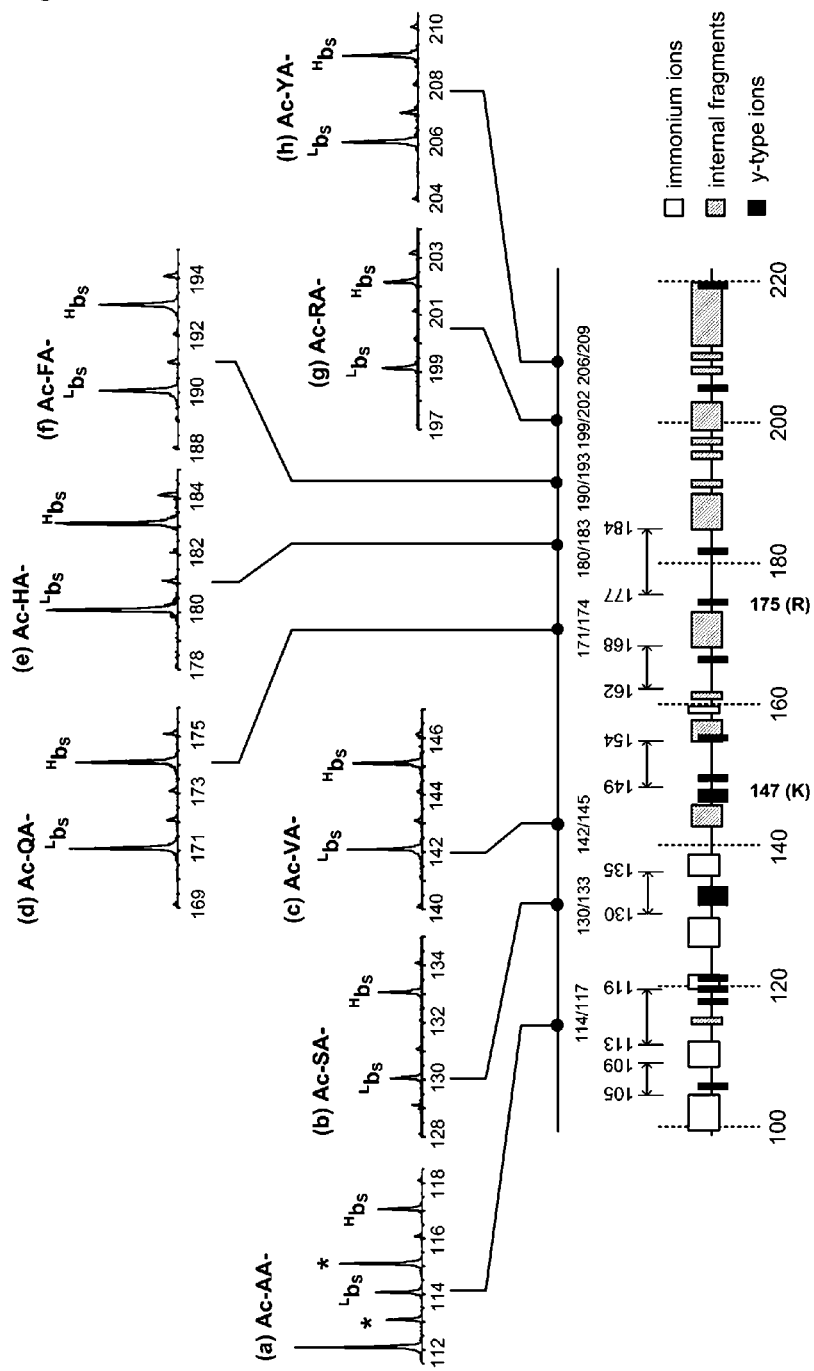
FIG. 10 is a diagram showing the quantitation signal mass window of FIG. 9, in which distribution of possible fragment ions at 220Th or below by tandem mass spectrometry of peptides is also shown. In the N-acetylated dipeptide MBIT reagent (Ac-Xxx-Ala), when Xxx having a mass-tunable group is (a) alanine, (b) serine, (c) valine, (d) glutamine, (e) histidine, (f) phenylalanine, (g) arginine, and (h) tyrosine, the results are shown.
Figure 13A:
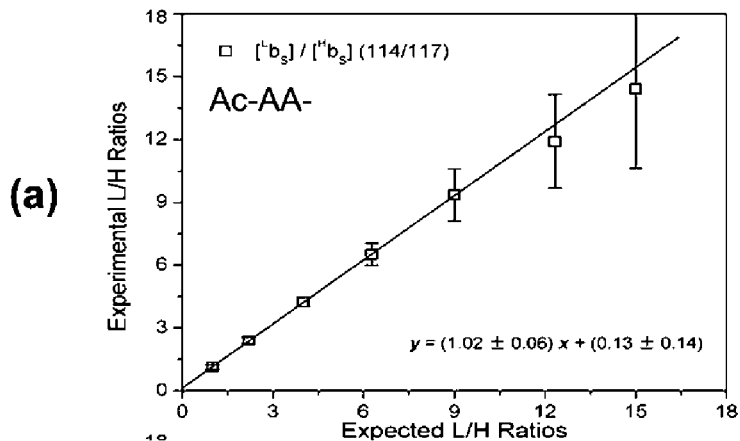
FIG. 13 is a diagram showing standard quantitation curve obtained by tandem mass spectrometry of the mixtures of different ratio of MBIT reagent-linked angiotensin II. In the N-acetylated dipeptide MBIT reagent (Ac-Xxx-Ala), when Xxx having a mass-tunable group is (a) alanine, (b) serine, (c) valine, (d) glutamine, (e) histidine, (f) phenylalanine, (g) arginine, and (h) tyrosine, the results are shown. Error bars stand for standard deviations from eight repeated experiments.
Figure 13B:
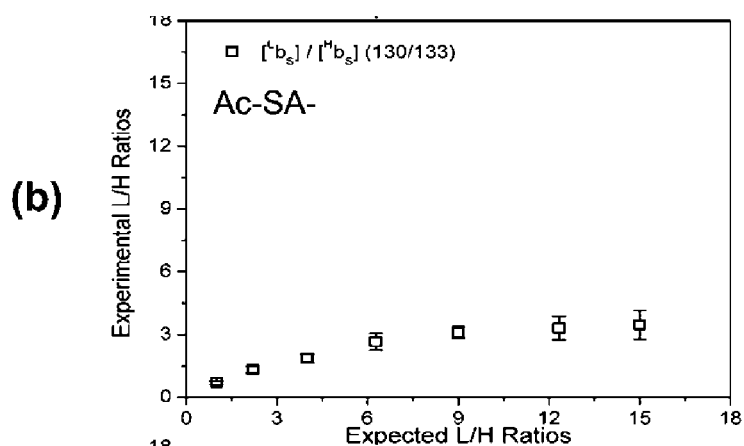
Figure 13C:
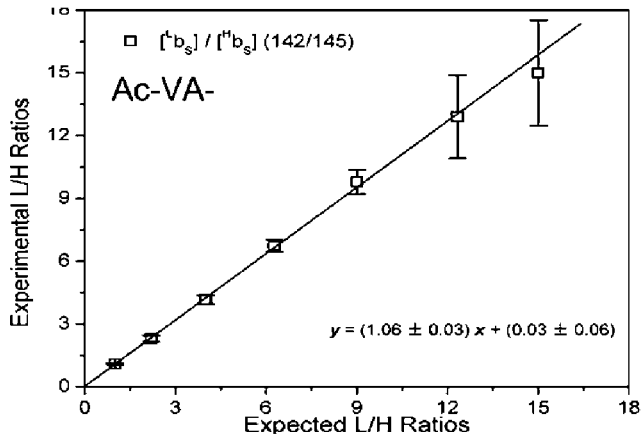
Figure 13D:
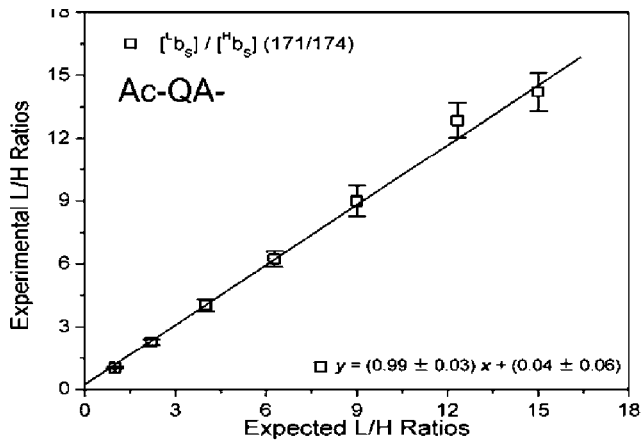
Figure 13E:
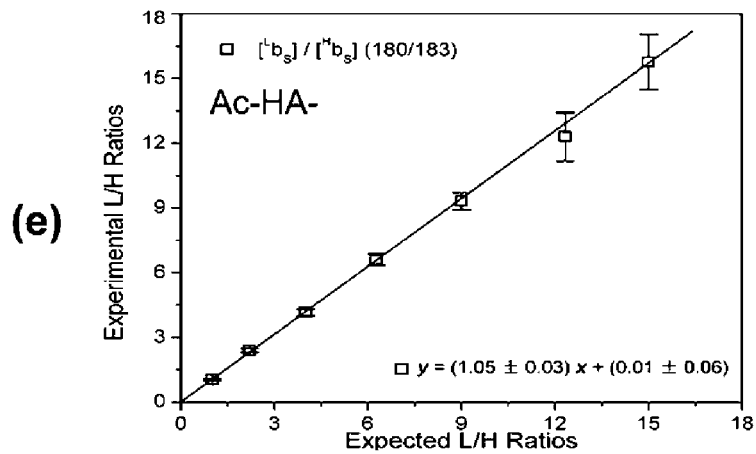
Figure 13F:
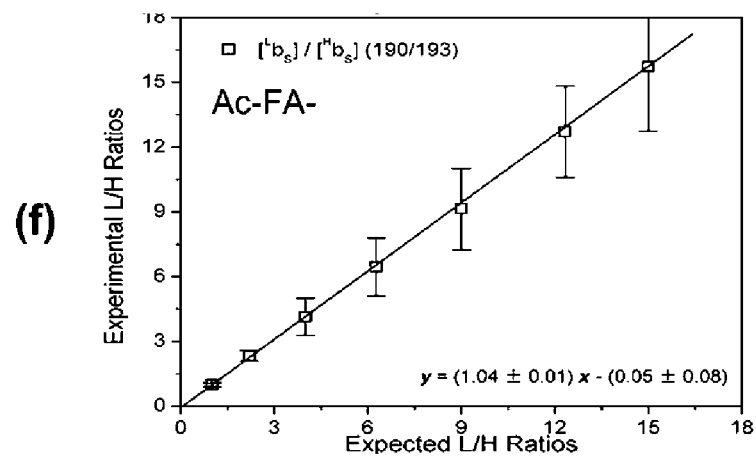
Figure 13G:
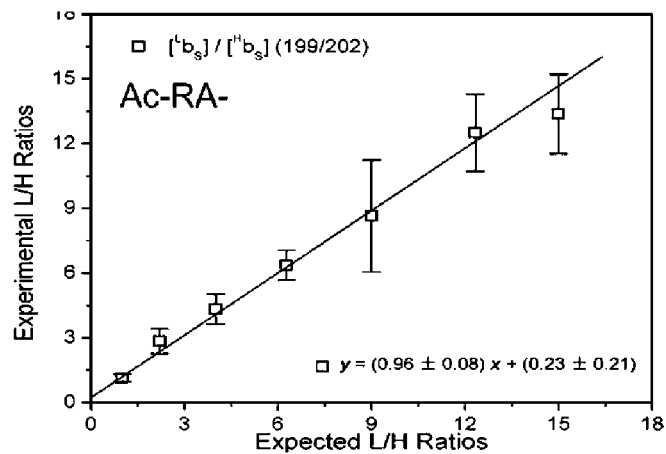
Figure 13H:
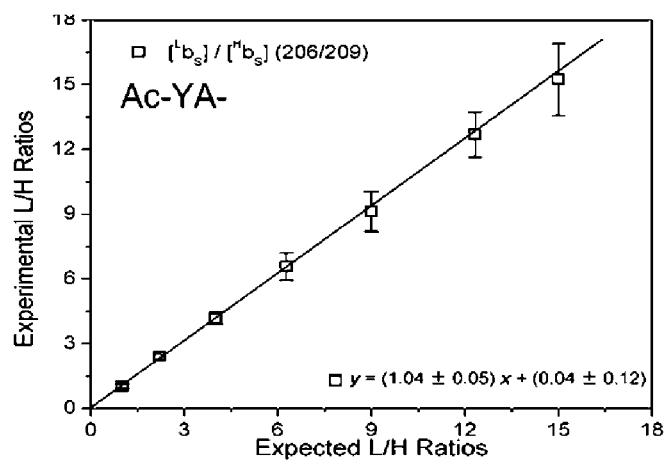

FIG. 10 is a diagram showing quantitation signal $^X b_S$ of each type of MBITs. As shown in FIG. 10, the $[^L b_S]/[^H b_S]$ ratio was found to be almost equal to the [L]/[H] ratio of 1/1. Ac-AA MBIT showed unknown chemical noise, which was presumably derived from peptide, near 114 and 117 Th where $^X b_S$ pair appeared. Ac-SA MBIT showed relatively weak signals, and its signal intensity ratio was not equal to the ratio of 1/1. However, other six different MBITs showed little chemical noise, and their signal intensity ratios were almost equal to the ratio of 1/1.

FIG. 11 is the result of CID spectra of MBIT-linked leucine enkephalin, in which (a) is the result of Ac-HA-linked leucine enkephalin, and (b) is the result of Ac-RA-linked leucine enkephalin. Like the CID results of MBIT-linked angiotensin II as described above, y-type ions were detected at the same region, irrespective of the types of MBIT reagents, but a- or b-type ions were detected at the different regions, according to the type of mass-tunable group. In addition, since Ac-RA-linked leucine enkephalin has N-terminal arginine side chain, the neutral $NH_3$-loss was detected in a- and b-type ions. Ac-HA- and Ac-RA-linked leucine enkephalins showed a great difference in fragment ion distribution, respectively, indicating that physical and chemical properties of target peptide could be tuned depending on the type of MBITs, and the mass-tunable group R T provided the tunability on quantitation signal mass and property of analyte.

FIG. 12 is a diagram showing the ratio of quantitation signal intensity of each MBIT reagent to total sum of all fragment ions intensities. For accurate quantitation, the intensity of quantitation signal $^X b_S$ ion should be strong, and additional dissociation of the quantitation signal ion should not occur. MBIT reagents having the mass-tunable group of glutamine or histidine side chain showed the strongest quantitation signals, and the intensity of additional fragment ion was weak, relative to the quantitation signal mass. When the mass-tunable group was a histidine side chain, quantitation signals were amplified five-fold or more than alanine side chain due to its strongest $^X b_S$ ion intensity. When the mass-tunable group was a glutamine side chain, $^X a_S$ ion generated by additional dissociation of $^X b_S$ showed the weakest intensity. These results indicated that MBIT having mass-tunable group of histidine or glutamine side chain achieved best performances in quantitation analysis of peptide and protein.

FIG. 13 is a diagram showing quantitation linearity in various MBITs, in which $^L$MBIT-linked angiotensin II and $^H$MBIT-linked angiotensin II were mixed in a various mixing ratio as described above, and experimental ratios and expected ratios were used to obtain quantitation linearity. It was found that except for Ac-SA MBIT, seven different MBITs showed excellent linearity in quantitation analysis of angiotensin II. In particular, Ac-QA MBIT having the mass-tunable group of glutamine side chain and Ac-HA MBIT having the mass-tunable group of histidine side chain showed the least standard deviation in observed ratios (within 20% of measured value) and excellent linearity, resulting from strong quantitation signal intensities of Ac-QA and Ac-HA MBITs. The results indicated that Ac-QA and Ac-HA MBITs showed excellent performance in quantitation analysis of peptide and protein. Ac-SA MBITs showed poor performance and no linearity, because the quantitation signal intensity in CID of Ac-SA MBIT-linked angiotensin II was weaker compared to those of other MBITs, and unexpected chemical noise was detected at 130 and 133 Th. The chemical noise was the same as that detected in angiotensin II labeled with no MBIT.

FIG. 14 is a diagram showing quantitation linearity of leucine enkephalin, resulting from Ac-HA MBIT- or Ac-RA MBIT-linked leucine enkephalin. Like the results of angiotensin II in FIG. 13, experimental ratios and expected ratios showed good quantitation linearity.

Figure 15:
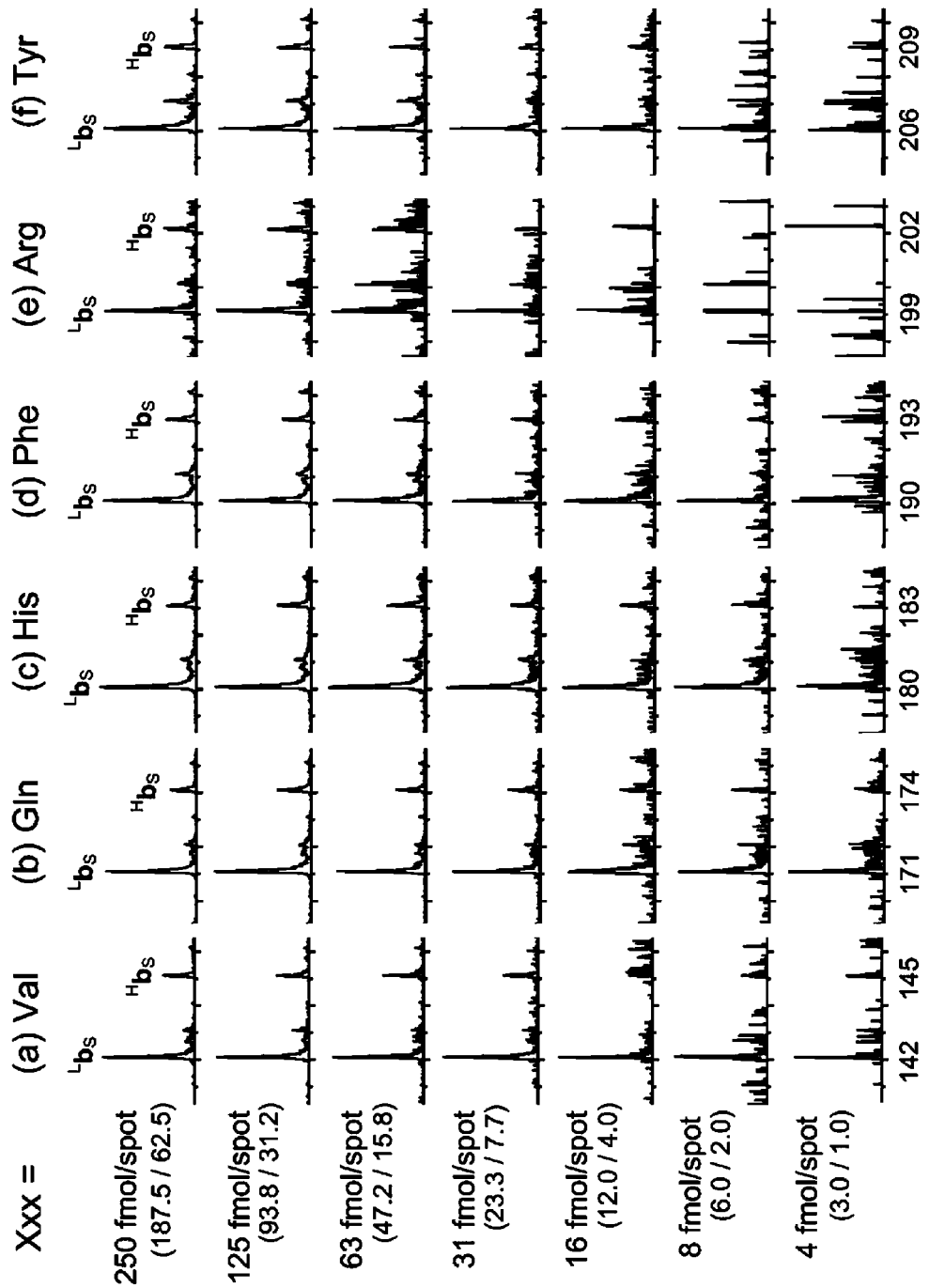
FIG. 15 is the results showing the detection limit of quantitation signal of the N-acetylated dipeptide MBIT-labeled analyte.
Figure 16A:
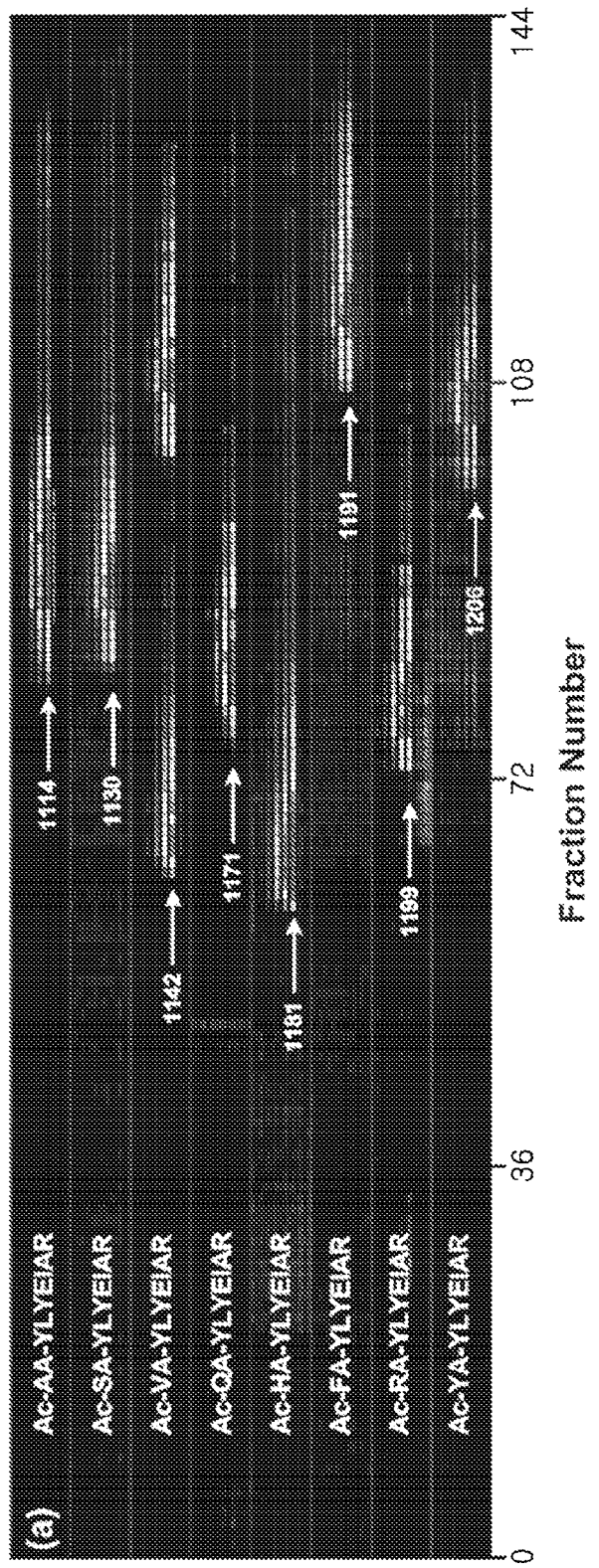
FIG. 16 is a diagram showing the results of liquid chromatography and tandem mass spectrometry of peptides, produced by enzymatic hydrolysis of the same amount of BSA (Bovine Serum Albumin) using trypsin, tagged with a pair of N-acetylated dipeptide MBIT reagents, and mixed with each other. The results show the quantitation of the peptide having a YLYEIAR sequence (SEQ ID NO:1).
Figure 16B:
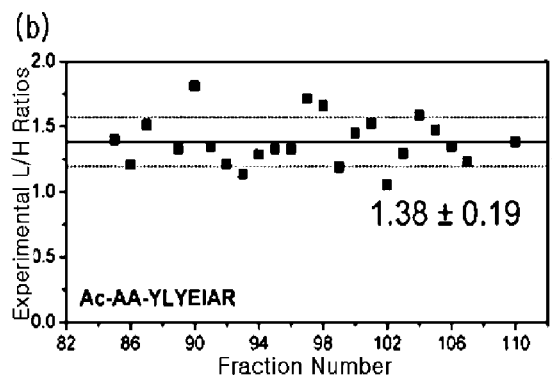
Figure 16F:
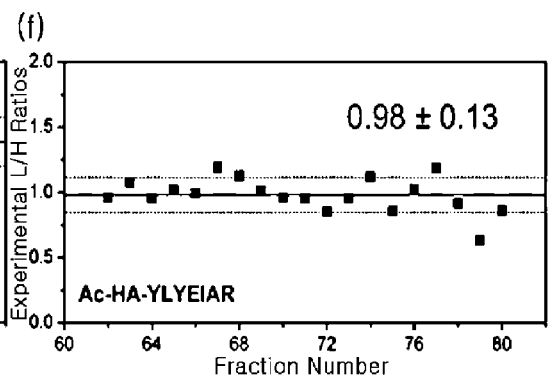
Figure 16C:
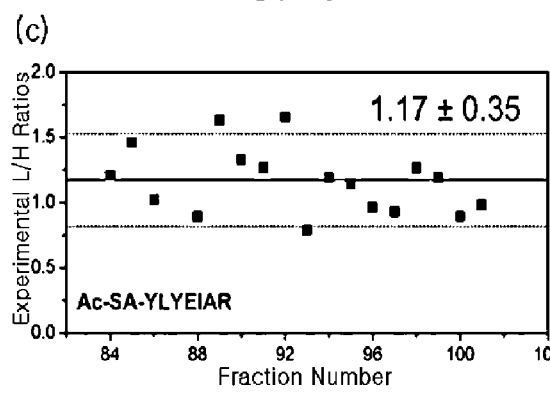
Figure 16G:
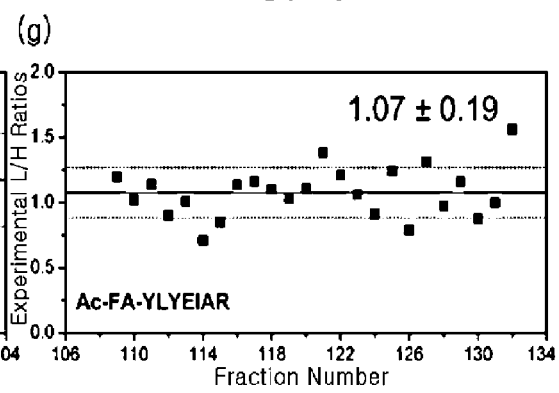
Figure 16D:
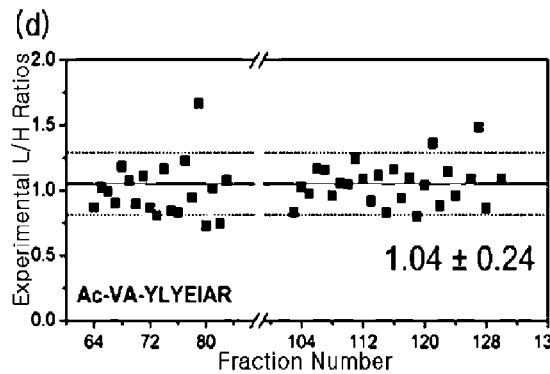
Figure 16H:
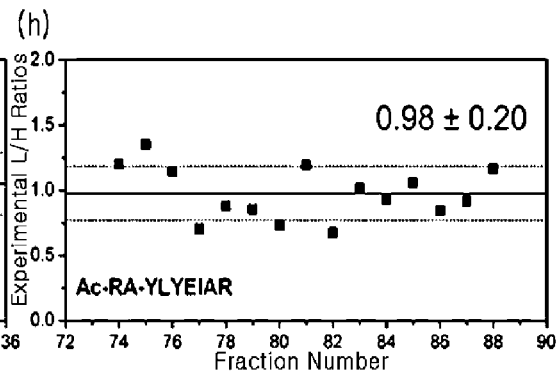

FIG. 15 is the results showing the detection limit of quantitation signal from N-acetylated dipeptide MBIT-labeled analyte. $^L$MBIT- and $^H$MBIT-labeled angiotensin II were mixed in a ratio of 3:1, and then tandem mass spectrometry was performed to show the quantitation signal mass ($b_S$) window. When Xxx having mass-tunable group is (a) valine, (b) glutamine, (c) histidine, (d) phenylalanine, (e) arginine, and (f) tyrosine in N-acetylated dipeptide MBIT reagents (Ac-Xxx-Ala), the detection limit of quantitation signal is shown.

250 fmol of the sample was loaded on a MALDI spot, and two-fold serial dilution was performed to observe the quantitation signal-to-noise ratio. It was found that a detection limit reached about 4-8 fmol. The detection limit corresponds to the detection limit of MALDI mass spectrometry. Thus, it can be expected that detection limit of MBIT reagents can be improved by using better equipment.

FIG. 16 is a diagram showing the results of liquid chromatography and tandem mass spectrometry of peptides, produced by enzymatic hydrolysis of the same amount of BSA (Bovine serum albumin) using trypsin, tagged with a pair of N-acetylated dipeptide MBIT reagents, and mixed with each other. The results show the quantitation of peptide having a YLYEIAR sequence. In FIG. 16, (a) shows the result of liquid chromatography of eight different pairs of MBIT-tagged YLYEIAR (SEQ ID NO:1) peptides. Also, FIG. 16 is a diagram showing the result of MALDI tandem mass spectrometry of each fraction detected from chromatography of pairs of MBIT-linked YLYEIARs in case that mass-tunable group is (b) alanine, (c) serine, (d) valine, (e) glutamine, (f) histidine, (g) phenylalanine, (h) arginine, and (i) tyrosine side chains. From the result of quantitation analysis, the mean and standard deviations are given. Since liquid chromatography is generally used for protein quantitation and sequencing, $^H$MBIT- and $^L$MBIT-linked peptides should be eluted at the same time in chromatography for favorable performance of MBIT in protein quantitation and sequencing. Each fraction of $^H$MBIT- and $^L$MBIT-linked peptides was found to have a constant mixing ratio, indicating that those peptides eluted at the same time in chromatography.

(b) Mass-Tunable Group of Ethyl($C_2$), Propyl($C_3$), Butyl ($C_4$), Pentyl($C_5$), Hexyl($C_6$), Heptyl($C_7$), or Octyl($C_8$)

Confirmation of Alkyl Group MBITs

Figure 18:
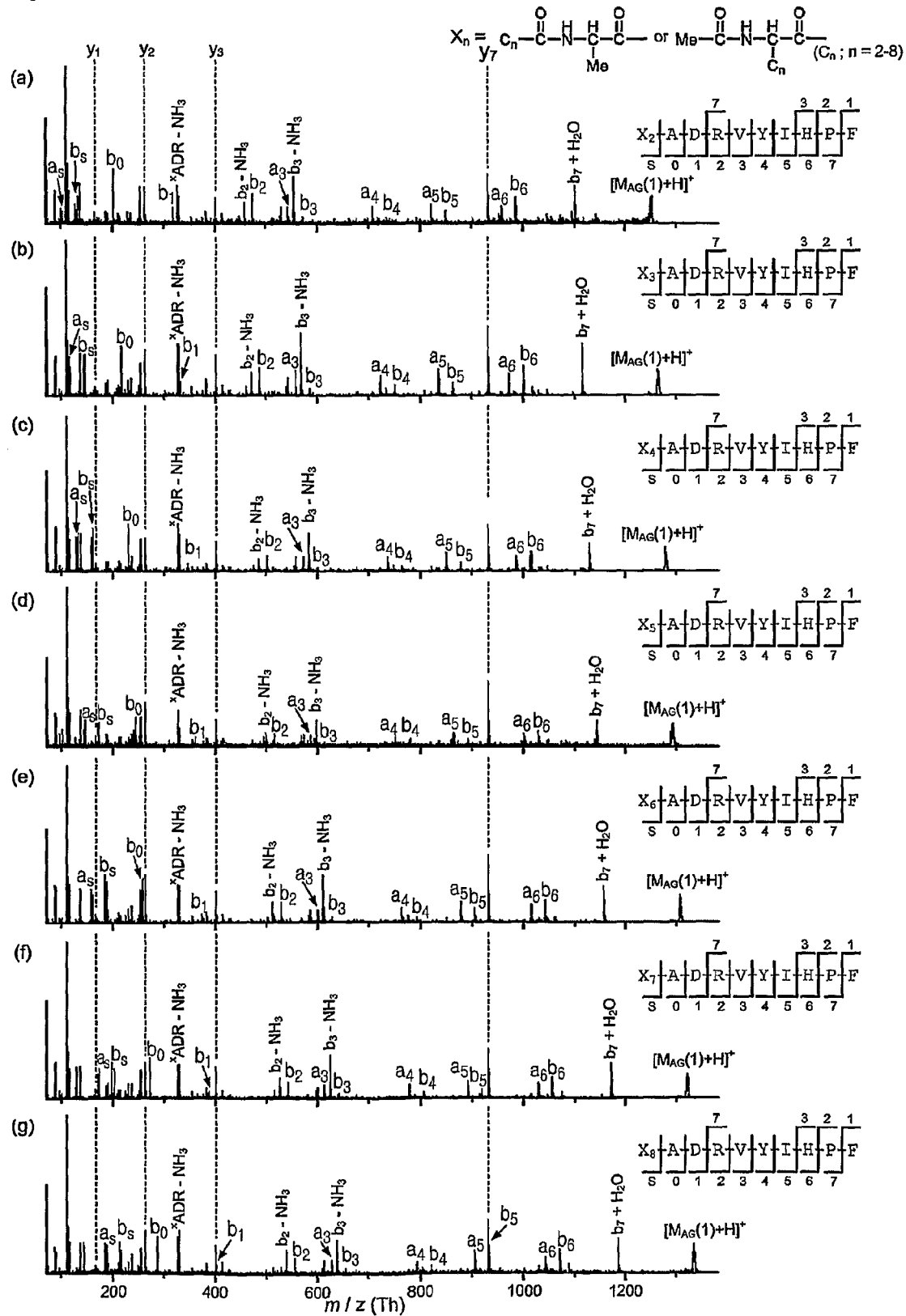
FIG. 18 is the results of MALDI tandem mass spectrometry of angiotensin II linked with seven pairs of alkyl group MBIT reagents, showing the results of tandem mass spectrometry of the mixtures of $^H$MBIT-linked peptide and $^L$MBIT-linked peptide (a mixing ratio of 1:1), and showing the collision-induced dissociation (CID) spectra of angiotensin II linked with MBITs having a mass-tunable group ($R_T=C_n$) of (a) ethyl ($C_2$), (b) propyl ($C_3$), (c) butyl ($C_4$), (d) pentyl ($C_5$), (e) hexyl ($C_6$), (f) heptyl ($C_7$), and (g) octyl ($C_8$). ($X_n$ is N-acetylated amino acid or N-acyl-Ala amino acid having a mass-tunable group of $C_n$).

In order to confirm alkyl group MBITs, angiotensin II (1045.5 Da) was labeled with each MBIT reagent to detect signal mass of $[M_{AG}(1)+H]^+$ ion (FIG. 17), and to perform tandem mass spectrometry (FIG. 18). $^L$MBIT and $^H$MBIT-linked angiotensin II appeared at the same mass. When the mass-tunable group was ethyl, propyl, butyl, pentyl, hexyl, heptyl, and octyl, $[M_{AG}(1)+H]^+$ ions were detected at 1247.7 Th, 1261.7 Th, 1275.7 Th, 1289.7 Th, 1303.7 Th, 1317.7 Th, and 1331.8 Th, respectively. When the mass-tunable group was ethyl, propyl, butyl, pentyl, hexyl, heptyl, and octyl, the tagging signature and quantitation signal mass appeared at 202 Th ($b_0$), 128 Th ($^Lb_S$), and 131 Th ($^Hb_S$), 216 Th ($b_0$), 142 Th ($^Lb_S$), and 145 Th ($^Hb_S$), 230 Th ($b_0$), 156 Th ($^Lb_S$), and 159 Th ($^Hb_S$), 244 Th ($b_0$), 170 Th ($^Lb_S$), and 173 Th ($^Hb_S$), 258 Th ($b_0$), 184 Th ($^Lb_S$), and 187 Th ($^Hb_S$), 272 Th ($b_0$), 198 Th ($^Lb_S$), and 201 Th ($^Hb_S$), and 286 Th ($b_0$), 212 Th ($^Lb_S$), and 215 Th ($^Hb_S$), respectively. The results indicated that alkyl group MBIT reagents having mass-tunable group of ethyl ($C_2$), propyl ($C_3$), butyl ($C_4$), pentyl ($C_5$), hexyl ($C_6$), heptyl ($C_7$), or octyl ($C_s$) were favorably synthesized.

Tandem Mass Spectrometry of Alkyl Group MBIT-linked Model Peptides

In order to confirm the reactivity of alkyl group MBIT reagents with peptides, angiotensin II (1045.5 Da) was linked with each MBIT reagent to perform mass spectrometry. FIG. 17 is the results of MALDI-mass spectrometry of angiotensin II linked with seven pairs of alkyl group MBIT reagents. The MALDI mass spectra of MBIT reagents having a mass-tunable group ($R_T=C_n$) of (a) ethyl ($C_2$), (b) propyl ($C_3$), (c) butyl ($C_4$), (d) pentyl ($C_5$), (e) hexyl ($C_6$), (f) heptyl ($C_7$), and (g) octyl ($C_s$) are shown. As shown in FIG. 17, when a mass-tunable group was ethyl, propyl, butyl, pentyl, hexyl, and heptyl, and octyl, signals were detected at 1247.7 Th, 1261.7 Th, 1275.7 Th, 1289.7 Th, 1303.7 Th, 1317.7 Th, and 1331.8 Th, respectively. Further, tagging signature and quantitation signal mass of each analyte were also analyzed by tandem mass spectrometry. Unreacted peptides or peptides linked with two or more MBITs were not observed, and angiotensin II linked with only one MBIT was observed, indicating successful coupling.

Further, to confirm the quantitation signal mass of the corresponding MBIT reagent, angiotensin II ions coupled with seven different MBIT reagents were subjected to MALDI tandem mass spectrometry. FIG. 18 is the results of tandem mass spectrometry of the mixtures of $^H$MBIT-linked peptide and $^L$MBIT-linked peptide (a mixing ratio of 1:1). FIG. 18($a$-$g$) shows CID spectra of angiotensin II-linked with MBITs having amass-tunable group ($R_T=C_n$) of ethyl ($C_2$), propyl ($C_3$), butyl ($C_4$), pentyl ($C_5$), hexyl ($C_6$), heptyl ($C_7$), and octyl ($C_8$), respectively. As expected from the values of FIG. 3($b$), when the mass-tunable group was ethyl, the tagging signature and quantitation signal mass appeared at 202 Th ($b_0$), 128 Th ($^Lb_S$), and 131 Th ($^Hb_S$), propyl at 216 Th ($b_0$), 142 Th ($^Lb_S$), and 145 Th ($^Hb_S$), butyl at 230 Th ($b_0$), 156 Th ($^Lb_S$), and 159 Th ($^Hb_S$), pentyl at 244 Th ($b_0$), 170 Th ($^Lb_S$), and 173 Th ($^Hb_S$), hexyl at 258 Th ($b_0$), 184 Th ($^Lb_S$), and 187 Th ($^Hb_S$), heptyl at 272 Th ($b_0$), 198 Th ($^Lb_S$), and 201 Th ($^Hb_S$), and octyl at 286 Th ($b_0$), 212 Th ($^Lb_S$), and 215 Th ($^Hb_S$). Since MBIT reagent was linked to the N-terminal primary amine, fragment y-type ions having C-terminal were detected at the same m/z values, irrespective of the types of MBIT reagents. In addition, all MBITs displayed similar fragment ion distribution in CID spectra. It can be seen that the length difference of each mass-tunable group does not affect the fragment ion distribution. The results indicate successful synthesis of alkyl group MBIT reagents and coupling with model peptides.

Figure 19:
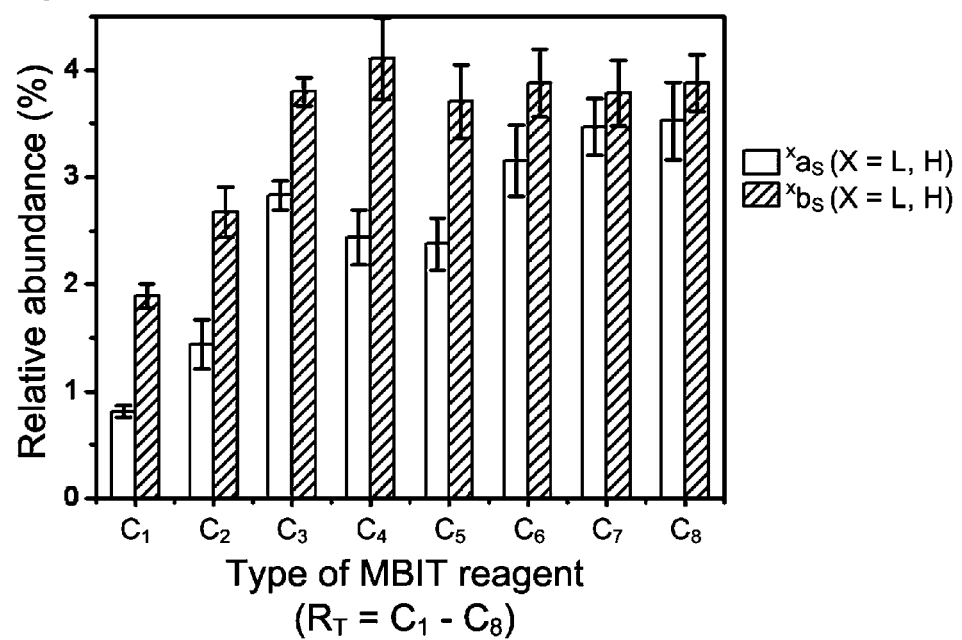
FIG. 19 is a diagram showing the ratio of quantitation signal intensity according to the alkyl mass-tunable group of each MBIT reagent relative to the total sum of all fragment ion intensities.

FIG. 19 is a diagram showing the ratio of quantitation signal intensity according to the alkyl mass-tunable group of each MBIT reagent relative to total sum of all fragment ion intensities. When the mass-tunable group was propyl to octyl, the relative intensity of $^Xb_S$ was 3.8%. When the mass-tunable group was methyl and ethyl, the relative intensity of $^Xb_S$ was 1.9% and 2.7%, respectively, which was lower than those of other MBITs. The intensity of $^Xa_S$ became stronger, as the length of mass-tunable group got longer.

FIG. 20 is a diagram showing comparison of quantitation linearity in various alkyl group MBITs, in which $^L$MBIT-linked angiotensin II and $^H$MBIT-linked angiotensin II were mixed in a various mixing ratio, and experimental ratios and expected ratios were used to obtain quantitation linearity.

FIG. 20($a$-$g$) shows the results of quantitation analysis of the MBIT quantitation signals, $^Xa_S$ (white circle) and $^Xb_S$ (black circle), when the mass-tunable group is ethyl, propyl, butyl, pentyl, hexyl, heptyl, and octyl. The dotted lines denote the results of experiments using $^Xa_S$, and the solid lines denote the results of experiments using $^Xb_S$. It was found that all MBITs used in the present invention showed excellent linearity in quantitation analysis of angiotensin II. The quantitation analysis using $^Xa_S$ showed the excellent linearity, similar to that of $^Xb_S$, indicating that $^Xa_S$ as well as $^Xb_S$ could be used for quantitation analysis.

Figure 21:
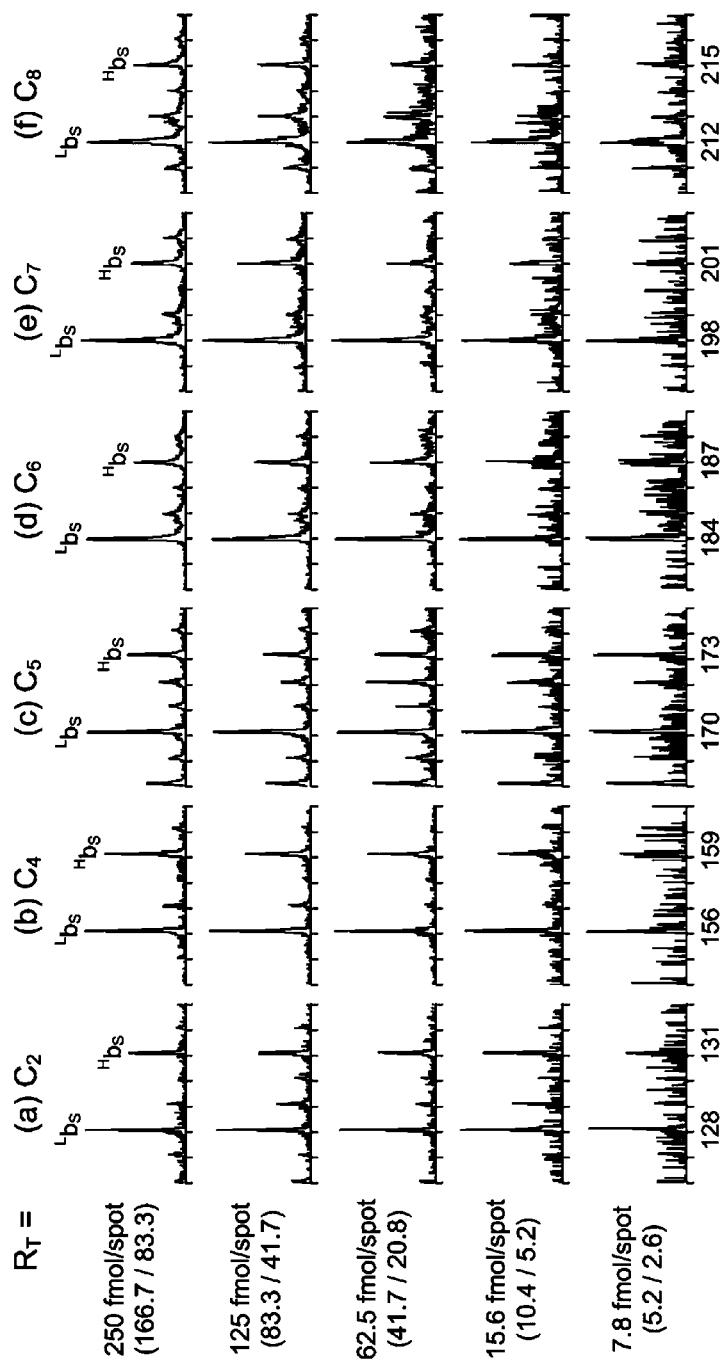
FIG. 21 is the results showing the detection limit of quantitation signal from alkyl group MBIT-labeled analyte. $^L$MBIT- and $^H$MBIT-labeled angiotensin II were mixed in a ratio of 2:1, and then concentration was continuously diluted two-fold. Tandem mass spectrometry was performed to show the quantitation signal mass ($b_S$) window. When the mass-tunable group ($R_T=C_n$) is (a) ethyl ($C_2$), (b) butyl ($C_4$), (c) pentyl($C_5$), (d) hexyl ($C_6$), (e) heptyl ($C_7$), and (f) octyl($C_8$), the detection limit of quantitation signal is shown.

FIG. 21 is the results showing the detection limit of quantitation signal from alkyl group MBIT-labeled analyte. $^L$MBIT- and $^H$MBIT-labeled angiotensin II were mixed in a ratio of 2:1, and then concentration was continuously diluted two-fold. Tandem mass spectrometry was performed to show the quantitation signal mass ($b_S$) window. When the mass-tunable group ($R_T=C_n$) is (a) ethyl ($C_2$), (b) butyl ($C_4$), (c) pentyl ($C_5$), (d) hexyl ($C_6$), (e) heptyl ($C_7$), and (f) octyl ($C_8$), the detection limit of quantitation signal is shown.

250 fmol of the sample was loaded on a MALDI spot, and two-fold serial dilution was performed to observe the quantitation signal-to-noise ratio. It was found that all samples had the detection limit of about 5 fmol. The detection limit corresponds to the detection limit of MALDI mass spectrometry. Thus, it can be expected that detection limit of MBIT reagents can be improved by using better equipment.

Figure 22:
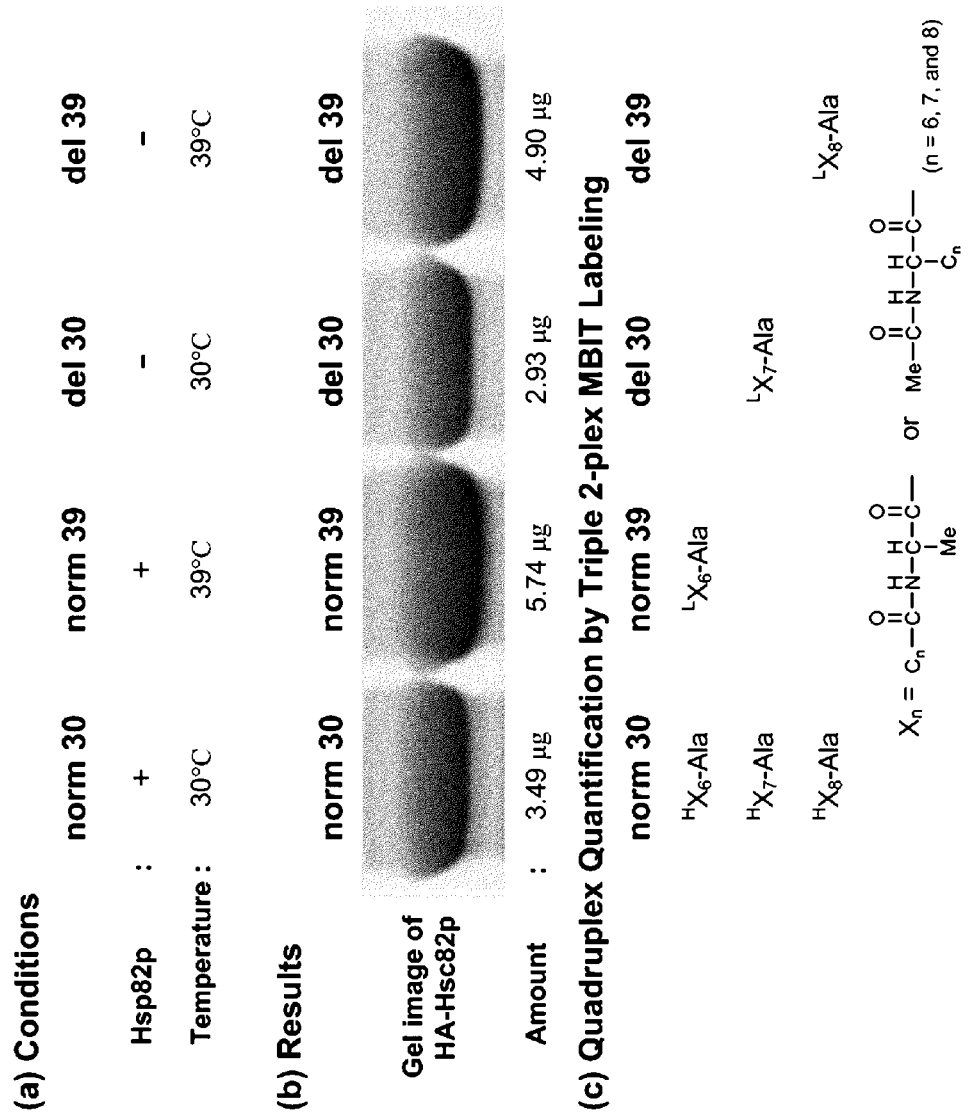
FIG. 22 is a diagram showing quantitation of hemmaglutinin (HA)-Hsc82 protein obtained from four different physiological states by using alkyl group MBIT reagents. Expression conditions of HA-Hsc82 protein are shown in (a), and HA-Hsc82 proteins expressed under the conditions, purified from cell lysates, separated by gel electrophoresis, and visualized by Sypro Ruby staining, as shown in (b). Gel bands of HA-Hsc82 proteins of four conditions were excised, enzymatically hydrolyzed with trypsin, and then conjugated to the alkyl group MBIT reagents as shown in (c). ($X_n$ is N-acetylated amino acid or N-acyl-Ala amino acid having a mass-tunable group of $C_n$).

FIG. 22 is a diagram showing quantitation of HA-Hsc82 protein obtained from four different physiological states and MBIT reagents used in each sample. Expression conditions of HA-Hsc82 protein are shown in (a). The norm 30 represents that yeast having both Hsp82 and Hsc82 proteins was cultured at 30° C., the norm 39 represents that yeast having both Hsp82 and Hsc82 proteins was cultured at 39° C., the del 30 represents that yeast deficient for Hsp82 protein was cultured at 30° C., and the del 39 represents that yeast deficient for Hsp82 protein was cultured at 39° C. HA-Hsc82 proteins expressed under those conditions were purified from cell lysates and then separated by gel electrophoresis. The expressed HA-Hsc82 proteins were visualized by Sypro Ruby staining, as shown in (b). According to the quantification result using a gel imaging system, norm 30 was 3.49 μg, norm 39 5.74 μg, del 30 2.93 μg, and del 39 4.90 μg. Protein bands of HA-Hsc82 proteins expressed under four different conditions were excised from the gel. After trypsin digestion, the peptides were coupled to MBIT reagents as shown in (c). At this time, norm 39 and $^{L}X_{6}$-Ala were reacted with each other, del 30 and $LX_{7}$-Ala, del 39 and $^{L}A_{8}$-Ala, norm 30 and $^{H}X_{6}$-Ala, $^{H}X_{7}$-Ala, and $^{H}X_{8}$-Ala ($X_{n}$, is N-acetylated amino acid or N-acyl-Ala amino acid having a mass-tunable group of $C_{n}$). The 1:1 mixtures of $^{L}$MBIT and $^{H}$MBIT were quantitated. When the mass-tunable group was hexyl, heptyl, and octyl, the expected ratios were 1.64, 0.84, and 1.40, respectively (norm 30: norm 39: del 30: del 39=1: 1.64: 0.84: 1.40).

Figure 23:
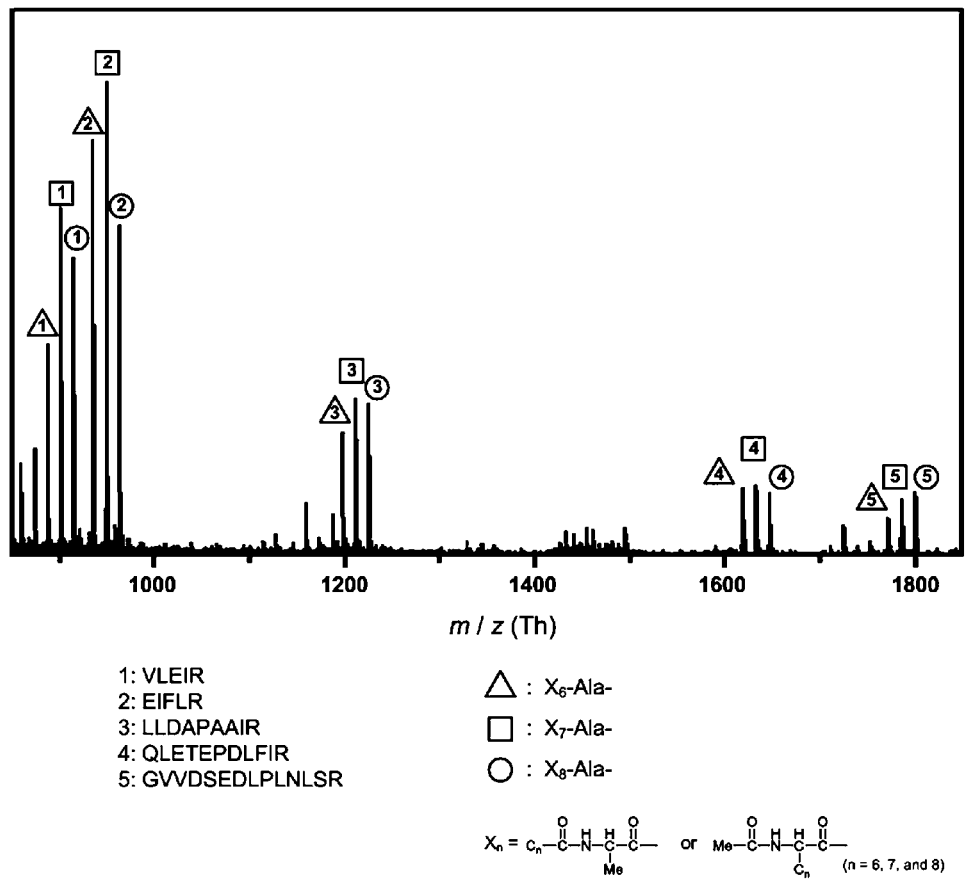
FIG. 23 is a diagram showing the results of mass spectrometry of six different types of analytes of FIG. 22(c) that have been mixed in equal amounts and purified by ZipTip. Each analyte was linked with MBIT reagents having a mass-tunable group ($R_T=C_n$) of hexyl (triangle), heptyl (square), and octyl (circle). Of the observed peptides, five peptides were used for tandem mass spectrometry. ($X_n$ is N-acetylated amino acid or N-acyl-Ala amino acid having a mass-tunable group of $C_n$).

FIG. 23 is a diagram showing the results of mass spectrometry of six different types of analytes of FIG. 22(c) that were mixed in the same amount and purified by ZipTip. Each analyte was linked with MBIT reagents having a mass-tunable group of hexyl (triangle), heptyl (square), and octyl (circle). In mass spectrum, the identical analytes were separated depending on mass difference of MBITs (14 Da). Of the observed peptides, five peptides were used for tandem mass spectrometry (VLEIR (SEQ ID NO:4), EIFLR (SEQ ID NO:5), LLDAPAAIR (SEQ ID NO:6), QLETEPDLFIR (SEQ ID NO:7), GVVDSEDLPLNLSR (SEQ ID NO:8)).

Figure 24:
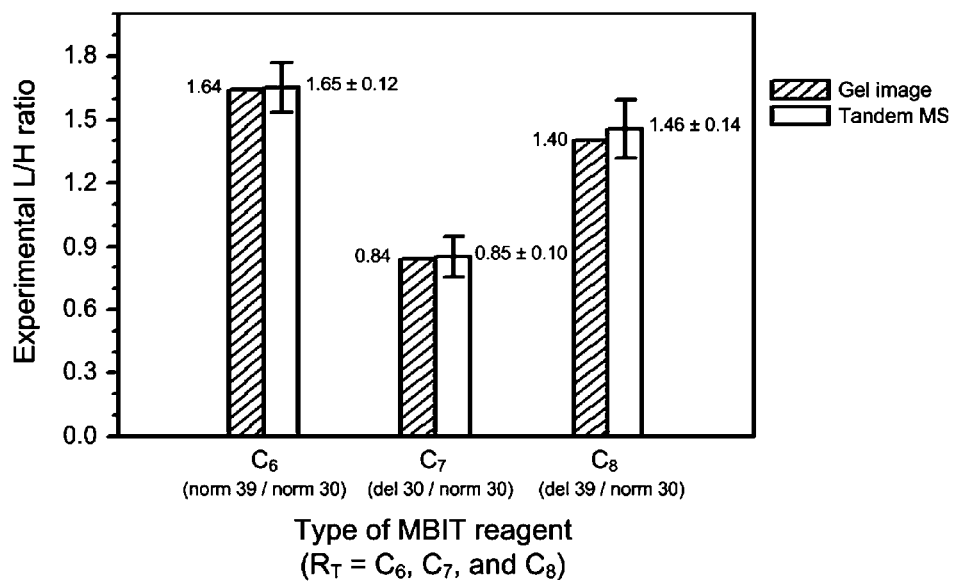
FIG. 24 is a diagram showing comparison of the quantitation results between gel imaging system and MALDI tandem mass spectrometry of alkyl group MBIT-linked analyte. The relative amounts of Hsc82 proteins obtained from four physiological states can be simultaneously quantitated using three pairs of alkyl group MBIT reagents.

FIG. 24 is a diagram showing comparison of the quantification results between gel imaging system and MALDI tandem mass spectrometry of alkyl group MBIT-linked analytes. The results from the alkyl group MBIT having a mass-tunable group of hexyl (norm 39/norm 30) gave a mean value of 1.65, which was 0.8% higher than that of gel imaging system. The results (del 30/norm 30) from using alkyl group MBIT having a mass-tunable group of heptyl gave a mean value of 0.85, which was 1.1% higher than that of gel imaging system. In addition, the results (del 39/norm 30) from the alkyl group MBIT having a mass-tunable group of octyl gave a mean value of 1.46, which was 4.0% higher than that of gel imaging system. It can be seen that the results are similar to those of gel imaging system. The relative amounts of Hsc82 proteins that were obtained from four physiological states could be simultaneously quantitated using three pairs of alkyl group MBIT reagents (norm 30: norm 39: del 30: del 39=1: 1.65: 0.85: 1.46).

FIG. 25 is the results of de novo sequencing from MALDI tandem mass spectrometry of five types of analytes that were labeled with MBIT having a mass-tunable group of hexyl, heptyl, and octyl. Underlined amino acids mean that their sequences were verified. Amino acids marked with star represent MBIT-labeled amino acids. Having the same composition, isoleucine is expressed as leucine.

The invention claimed is:

1. A variable mass labeling reagent represented by the following Formula 1:

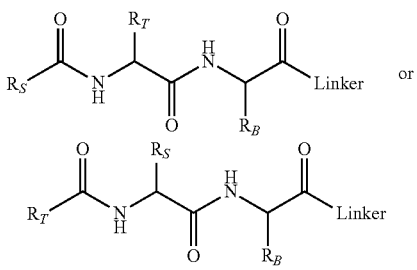

[Formula 1]

wherein $R_S$ and $R_B$ are each straight or branched chain $C_1$-$C_{18}$ alkyl; at least one of $R_S$ and $R_B$ contains one or more deuterium atoms; $R_T$ is a side chain of an amino acid selected from the group consisting of serine (Ser), histidine (His), glutamine (Gln), phenylalanine (Phe), arginine (Arg) and tyrosine (Tyr), or a straight or branched $C_2$-$C_{18}$ alkyl; and Linker is selected from the group consisting of hydroxy group, N-hydroxysuccinimidyl group, N-hydroxysulfosuccinimidyl group, benzotriazol-1-yloxyl group, pentahalobenzyl group and 4-nitrophenyl group, with the proviso that $R_S$ and $R_B$ are composed of alkyl having the same number of carbon atoms, but different numbers of deuterium atoms.

2. The variable mass labeling reagent according to claim 1, wherein $R_S$ and $R_B$ are each methyl.

3. The variable mass labeling reagent according to claim 2, wherein (a) $R_S$ is $CH_3$, and $R_B$ is $CD_3$; or (b) $R_S$ is $CD_3$, and $R_B$ is $CH_3$.

4. The variable mass labeling reagent according to claim 1, wherein the $R_T$ is straight or branched chain ethyl, propyl, butyl, pentyl, hexyl, heptyl, or octyl.

5. A set of variable mass labeling reagents, comprising two or more of variable mass labeling reagents represented by Formula 1 of claim 1.

6. The set of variable mass labeling reagents according to claim 5, wherein each of $R_S$ and $R_B$ in two or more variable mass labeling reagents contains a different number of deuterium atoms, and two or more variable mass labeling reagents contain the same number of deuterium atoms.

7. A multiplexed set of variable mass labeling reagents, comprising two or more sets of variable mass labeling reagents of claim 5.

8. A mixture comprising an analyte labeled with the variable mass labeling reagents of claim 1, a salt thereof, or a hydrate thereof 9. The mixture according to claim 8, wherein the analyte is a protein, a carbohydrate or a lipid.

10. The mixture according to claim 8, wherein the analyte is a peptide.

11. The mixture according to claim 8, wherein the analyte is a nucleic acid or a derivative thereof.

12. The mixture according to claim 8, wherein the analyte is a steroid.

13. An analysis method for simultaneous peptide sequencing and quantitation, comprising:

coupling one or more peptides with the set of variable mass labeling reagents of claim 5 to generate variable mass labeling reagent-linked peptides; and quantitating and sequencing the peptide(s) by fragmentation of the variable mass labeling reagent-linked peptides.

14. The analysis method for simultaneous peptide sequencing and quantitation according to claim 13, wherein the fragmentation for quantitation is performed by tandem mass spectrometry.

15. The analysis method for simultaneous peptide sequencing and quantitation according to claim 14, wherein the quantitation signal mass window is shifted by changing $R_T$ of the labeling reagent in the tandem mass spectrometry.

16. The analysis method for simultaneous peptide sequencing and quantitation according to claim 15, wherein the quantitation signal is one or more internal fragment ions selected from the group consisting of $b_S$ ion, $a_S$ ion, $y_S$ ion, and internal fragment ions containing $R_B$.

17. The analysis method for simultaneous peptide sequencing and quantitation according to claim 13, wherein
   1) in case that the $R_T$ is a serine side chain, the quantitation signal mass ($b_S$) appears at 130 and 133 Th, other quantitation signal mass ($a_S$) appears at 102 and 105 Th, and the tagging signature ($b_0$) is 204 Th,
   2) in case that the $R_T$ is a valine side chain, the quantitation signal mass ($b_S$) appears at 142 and 145 Th, other quantitation signal mass ($a_S$) appears at 114 and 117 Th, and the tagging signature ($b_0$) is 216 Th,
   3) in case that the $R_T$ is a glutamine side chain, the quantitation signal mass ($b_S$) appears at 171 and 174 Th, other quantitation signal mass ($a_S$) appears at 143 and 146 Th, and the tagging signature ($b_0$) is 245 Th,
   4) in case that the $R_T$ is a histidine side chain, the quantitation signal mass ($b_S$) appears at 180 and 183 Th, other quantitation signal mass ($a_S$) appears at 152 and 155 Th, and the tagging signature ($b_0$) is 254 Th,
   5) in case that the $R_T$ is a phenylalanine side chain, the quantitation signal mass ($b_S$) appears at 190 and 193 Th, other quantitation signal mass ($a_S$) appears at 162 and 165 Th, and the tagging signature ($b_0$) is 264 Th,
   6) in case that the $R_T$ is an arginine side chain, the quantitation signal mass ($b_S$) appears at 199 and 202 Th, other quantitation signal mass ($b_S$-$NH_3$) appears at 182 and 185 Th, and the tagging signature ($b_0$) is 273 Th, or
   7) in case that the $R_T$ is a tyrosine side chain, the quantitation signal mass ($b_S$) appears at 206 and 209 Th, other quantitation signal mass ($a_S$) appears at 178 and 181 Th, and the tagging signature ($b_0$) is 280 Th.

18. The analysis method for simultaneous peptide sequencing and protein quantitation according to claim 13, wherein
   1) in case that the $R_T$ is an ethyl group, the quantitation signal mass ($b_S$) appears at 128 and 131 Th, other quantitation signal mass ($a_S$) appears at 100 and 103 Th, and the tagging signature is 202 Th,
   2) in case that the $R_T$ is a straight or branched propyl group, the quantitation signal mass ($b_S$) appears at 142 and 145 Th, other quantitation signal mass ($a_S$) appears at 114 and 117 Th, and the tagging signature ($b_0$) is 216 Th,
   3) in case that the $R_T$ is a straight or branched butyl group, the quantitation signal mass ($b_S$) appears at 156 and 159 Th, other quantitation signal mass ($a_S$) appears at 128 and 131 Th, and the tagging signature ($b_0$) is 230 Th,
   4) in case that the $R_T$ is a straight or branched pentyl group, the quantitation signal mass ($b_S$) appears at 170 and 173 Th, other quantitation signal mass ($a_S$) appears at 142 and 145 Th, and the tagging signature ($b_0$) is 244 Th,
   5) in case that the $R_T$ is a straight or branched hexyl group, the quantitation signal mass ($b_S$) appears at 184 and 187 Th, other quantitation signal mass ($a_S$) appears at 156 and 159 Th, and the tagging signature ($b_0$) is 258 Th,
   6) in case that the $R_T$ is a straight or branched heptyl group, the quantitation signal mass ($b_S$) appears at 198 and 201 Th, other quantitation signal mass ($a_S$) appears at 170 and 173 Th, and the tagging signature ($b_0$) is 272 Th, or
   7) in case that the $R_T$ is a straight or branched octyl group, the quantitation signal mass ($b_S$) appears at 212 and 215 Th, other quantitation signal mass ($a_S$) appears at 184 and 187 Th, and the tagging signature ($b_0$) is 286 Th.

19. An analysis method for simultaneous peptide sequencing and quantitation, comprising:
   coupling peptides in multiple samples with the multiplexed set of variable mass labeling reagents of claim 7 to generate variable mass labeling reagent-linked peptides, and
   quantitating and sequencing the peptides by fragmentation of the variable mass labeling reagent-linked peptides.

20. The analysis method for simultaneous peptide sequencing and quantitation of claim 19, further comprising separately quantitating the ratio of one sample and other different samples, wherein
   1) in case that the RT is a serine side chain, the quantitation signal mass ($b_S$) appears at 130 and 133 Th, other quantitation signal mass ($a_S$) appears at 102 and 105 Th, and the tagging signature ($b_0$) is 204 Th,
   2) in case that the RT is a valine side chain, the quantitation signal mass ($b_S$) appears at 142 and 145 Th, other quantitation signal mass ($a_S$) appears at 114 and 117 Th, and the tagging signature ($b_0$) is 216 Th,
   3) in case that the RT is a glutamine side chain, the quantitation signal mass ($b_S$) appears at 171 and 174 Th, other quantitation signal mass ($a_S$) appears at 143 and 146 Th, and the tagging signature ($b_0$) is 245 Th,
   4) in case that the RT is a histidine side chain, the quantitation signal mass ($b_S$) appears at 180 and 183 Th, other quantitation signal mass ($a_S$) appears at 152 and 155 Th, and the tagging signature ($b_0$) is 254 Th,
   5) in case that the RT is a phenylalanine side chain, the quantitation signal mass ($b_S$) appears at 190 and 193 Th, other quantitation signal mass ($a_S$) appears at 162 and 165 Th, and the tagging signature ($b_0$) is 264 Th,
   6) in case that the RT is an arginine side chain, the quantitation signal mass ($b_S$) appears at 199 and 202 Th, other quantitation signal mass ($b_S$-$NH_3$) appears at 182 and 185 Th, and the tagging signature ($b_0$) is 273 Th, or
   7) in case that the RT is a tyrosine side chain, the quantitation signal mass ($b_S$) appears at 206 and 209 Th, other quantitation signal mass ($a_S$) appears at 178 and 181 Th, and the tagging signature ($b_0$) is 280 Th.

* * * * *